(12) United States Patent
Heidelbaugh et al.

(10) Patent No.: US 9,572,792 B2
(45) Date of Patent: Feb. 21, 2017

(54) COUMARIN COMPOUNDS AS RECEPTOR MODULATORS WITH THERAPEUTIC UTILITY

(71) Applicant: Allergan, Inc., Irvine, CA (US)

(72) Inventors: Todd M. Heidelbaugh, Fountain Valley, CA (US); John R. Cappiello, Irvine, CA (US); Phong X. Nguyen, Placentia, CA (US); Dario G. Gomez, Laguna Niguel, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/729,969

(22) Filed: Jun. 3, 2015

(65) Prior Publication Data

US 2015/0265573 A1  Sep. 24, 2015

Related U.S. Application Data

(63) Continuation of application No. 13/502,980, filed as application No. PCT/US2010/053363 on Oct. 20, 2010, now Pat. No. 9,073,888.

(60) Provisional application No. 61/254,236, filed on Oct. 23, 2009.

(51) Int. Cl.
| | | |
|---|---|---|
| *A61K 31/365* | (2006.01) |
| *A61K 31/366* | (2006.01) |
| *A61K 31/37* | (2006.01) |
| *C07D 311/16* | (2006.01) |
| *C07D 311/18* | (2006.01) |
| *C07D 405/12* | (2006.01) |
| *A61K 31/4025* | (2006.01) |
| *A61K 31/4433* | (2006.01) |
| *A61K 31/453* | (2006.01) |
| *A61K 31/501* | (2006.01) |

(52) U.S. Cl.
CPC ............. *A61K 31/37* (2013.01); *A61K 31/365* (2013.01); *A61K 31/366* (2013.01); *A61K 31/4025* (2013.01); *A61K 31/4433* (2013.01); *A61K 31/453* (2013.01); *A61K 31/501* (2013.01); *C07D 311/16* (2013.01); *C07D 311/18* (2013.01); *C07D 405/12* (2013.01)

(58) Field of Classification Search
CPC ..... A61K 31/365; A61K 31/366; A61K 31/37
See application file for complete search history.

(56) References Cited

U.S. PATENT DOCUMENTS 9,073,888 B2 * 7/2015 Heidelbaugh ........ C07D 311/16
2006/0148834 A1   7/2006 Xu

FOREIGN PATENT DOCUMENTS

WO    2007-115820 A1   10/2007
WO    WO2008-092930    8/2008

OTHER PUBLICATIONS

Ailin, Liu, Drug Screening for Influenza Neuraminidase Inhibitors, Science in China Ser. C Life Sciences 2005, Jan. 1, 2005, 1-5, 48 (1), Science in China Press, US.
Dross, L.C. et al, Rules for the Nomenclature of Organic Chemistry, Section E: Stereochemistry, Pure & Appl. Chem., 1976, 45, 1-30.
Hale, Jeffrey J., Potent S1P receptor agonists replicate the pharmacologic actions of the novel immune modulator FTY720, Bioorganic & Medicinal Chemistry Letters, 2004, 14, 3351-3355.
Patent Cooperation Treaty, Notification of Transmittal of the International Search Report and the Written Opinion of the International Searching Authority, or the Declaration, Form PCT/ISA/220, Int. App. PCT/US2010/053363, Apr. 19, 2011, p. 11.
Stahl, Heinrich et al, Handbook of Pharmaceutical Salts, Verlag Helvetica Chimica Acta—Zurich, 2002, 329-345.

* cited by examiner

*Primary Examiner* — Yong Chong
(74) *Attorney, Agent, or Firm* — Barbara C. Potts

(57) ABSTRACT

The present invention relates to novel 2-oxo-2H-chromene-3-carboxamide derivatives, processes for preparing them, pharmaceutical compositions containing them and their use as pharmaceuticals as modulators of sphingosine-1-phosphate receptors.

5 Claims, 1 Drawing Sheet

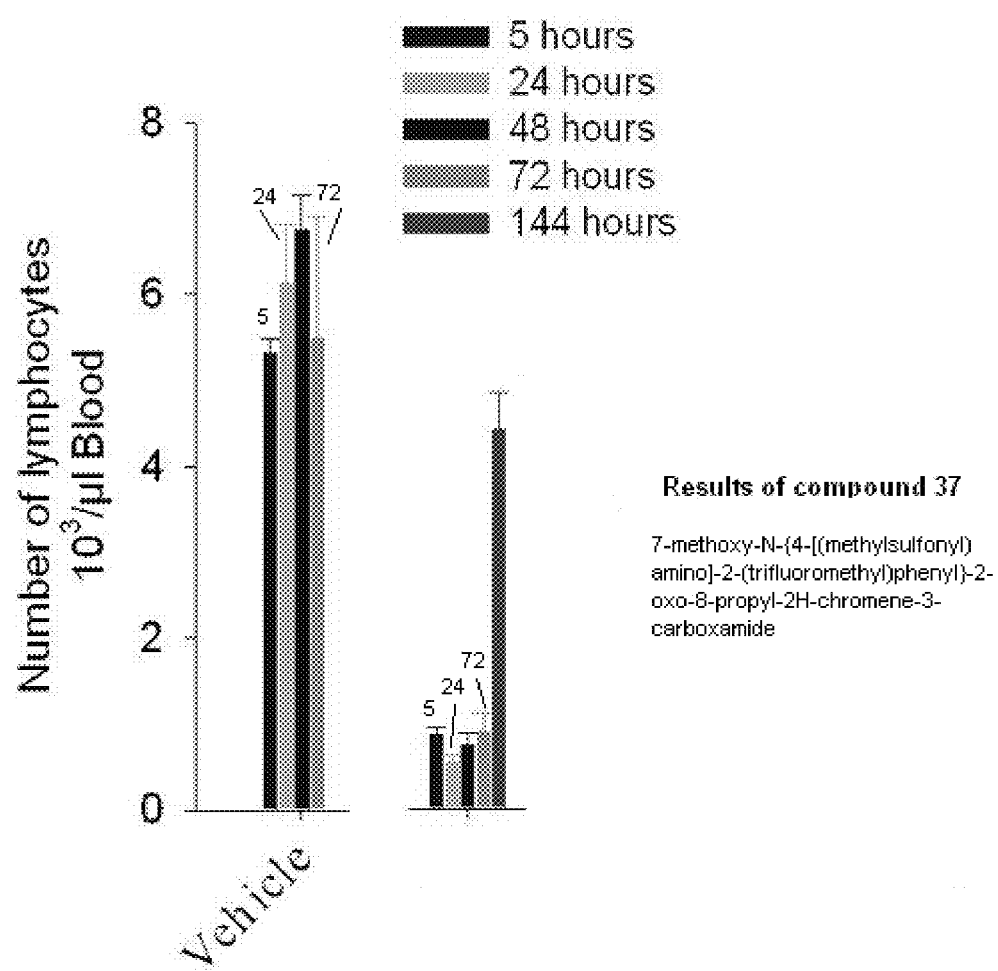

COUMARIN COMPOUNDS AS RECEPTOR MODULATORS WITH THERAPEUTIC UTILITY

CROSS REFERENCE TO RELATED APPLICATIONS

This application is a continuation of U.S. Nonprovisional application Ser. No. 13/502,980 filed on Sep. 11, 2012, which is a national stage application under 35 U.S.C. §371 of PCT application PCT/US2010/53363, filed on Oct. 20, 2010, which claims the benefit of U.S. Provisional Application Ser. No. 61/254,236 filed on Oct. 23, 2009, each of which is hereby incorporated by reference in its entirety.

FIELD OF THE INVENTION

The present invention relates to novel 2-oxo-2H-chromene-3-carboxamide derivatives, processes for preparing them, pharmaceutical compositions containing them and their use as pharmaceuticals as modulators of sphingosine-1-phosphate receptors. The invention relates specifically to the use of these compounds and their pharmaceutical compositions to treat disorders associated with sphingosine-1-phosphate 1 (S1P1) receptor modulation.

BACKGROUND OF THE INVENTION

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular diseases. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

International patent application WO2008/092930 A1 discloses Chromene S1P1 receptor antagonists.

International patent application WO2007/115820 A1 discloses Chromen-2-one derivatives.

United States Patent Application Publication US2006/0148834 A1 discloses coumarin derivatives, their carboxamides, pharmaceutical compositions containing them and their uses.

SUMMARY OF THE INVENTION

We have now discovered a group of novel compounds which are potent and selective sphingosine-1-phosphate modulators. As such, the compounds described herein are useful in treating a wide variety of disorders associated with modulation of sphingosine-1-phosphate receptors. The term "modulator" as used herein, includes but is not limited to: receptor agonist, antagonist, inverse agonist, inverse antagonist, partial agonist, partial antagonist.

This document describes compounds of Formula I, which have sphingosine-1-phosphate receptor biological activity. The compounds in accordance with the present invention are thus of use in medicine, for example in the treatment of humans with diseases and conditions that are alleviated by S1P modulation, and in particular use as S1P1 agonists or antagonists (functional antagonists).

In one aspect the invention provides a compound having Formula I or a pharmaceutically acceptable salt thereof or stereoisomeric forms thereof, and the geometrical isomers, enantiomers, diastereoisomers, tautomers, zwitterions and pharmaceutically acceptable salts thereof:

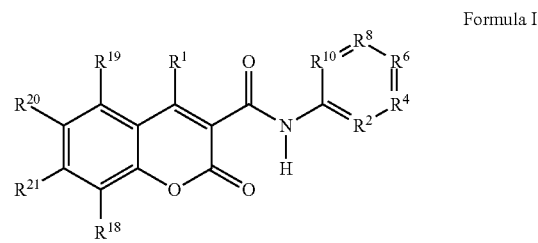

Formula I wherein:
$R^1$ is hydrogen, halogen or $C_{1-6}$ alkyl;
$R^2$ is $CR^3$ or N;
$R^3$ is hydrogen, halogen, $O(C_{1-6}$ alkyl), $S(C_{1-6}$ alkyl), cyano, aldehyde, heterocycle, $C_{1-6}$ alkyl or hydroxyl;
$R^4$ is $CR^5$ or N;
$R^5$ is hydrogen, halogen, hydroxyl or non-substituted $C_{1-6}$ alkyl;
$R^6$ is $CR^7$ or N;
$R^7$ is $-NHR^{12}$, $-S(O)_2R^{14}$, $-C(O)NHR^{16}$, $-OR^{17}$, hydrogen, halogen, phosphonic acid, boronic acid, $-CH_2-OH$, $-CH_2-S(O)_2CH_3$, $-(CH_2)_a-NH-(CH_2)_b-O_c-P(O)(OH)_2$, $-(CH_2)_d-C(NH_2)(CH_2OH)(CH_2-O-P(O)(OH)_2)$, $-(CH_2)_e-C(NH_2)(CH_3)(CH_2-O-P(O)(OH)_2)$; or $-(CH_2)_f-NH-(CH_2)_g-SO_3H$;
a is 1 or 2;
b is 2 or 3;
c is 0 or 1;
d is 0 or 1;
e is 0 or 1;
f is 0 or 1;
g is 2 or 3;
$R^8$ is $CR^9$ or N;
$R^9$ is hydrogen, halogen, non-substituted $C_{1-6}$ alkyl or hydroxyl;
$R^{10}$ is $CR^{11}$ or N;
$R^{11}$ is hydrogen, halogen or $C_{1-6}$ alkyl;
$R^{12}$ is hydrogen, $C_{1-6}$ alkyl, $-C(O)R^{13}$, $-S(O)_2(C_{1-3}$ alkyl) or heterocycle;
$R^{13}$ is amino or $C_{1-6}$ alkyl;
$R^{14}$ is $C_{1-4}$ alkyl, $NHR^{15}$ or hydroxyl;
$R^{15}$ is hydrogen or $C_{1-6}$ alkyl;
$R^{16}$ is hydrogen or $C_{1-6}$ alkyl;
$R^{17}$ is hydrogen, $C_{1-6}$ alkyl or $-S(O)_2(C_{1-3}$ alkyl);
$R^{18}$ is $C_{2-4}$ alkyl or $-OC_{2-4}$ alkyl;
$R^{19}$ is hydrogen, halogen or $C_{1-6}$ alkyl;
$R^{20}$ is hydrogen, halogen or $C_{1-6}$ alkyl; and
$R^{21}$ is $-OC_{1-4}$ alkyl.

The term "alkyl", as used herein, refers to saturated, monovalent or divalent hydrocarbon moieties having linear or branched moieties or combinations thereof and containing 1-8 carbon atoms, preferably 1-6 carbon atoms and more preferable 1-4 carbon atoms. One methylene (—$CH_2$—) group, of the alkyl can be replaced by oxygen, sulfur, sulfoxide, nitrogen, carbonyl, carboxyl, sulfonyl, or by a divalent ($C_{3-6}$ cycloalkyl). Alkyl moieties can optionally be substituted by halogen, hydroxyl, cycloalkyl, amino, non-aromatic heterocycles, carboxylic acid, phosphonic acid groups, sulphonic acid groups, phosphoric acid. Usually, in the present case, alkyl groups are methyl, ethyl, iso-propyl, 1-methylsulfanyl, trifluoromethyl, methylsulfanyl, isopropyldifluoro, n-propyl, propylsulphonic acid, 1,1,1,2,2 pentafluoroethyl, 3(ethylamino)cyclobutylphosphonic acid. Preferred alkyl groups are methyl, ethyl, n-propyl, iso-propyl, trifluoromethyl.

The term "cycloalkyl", as used herein, refers to a monovalent or divalent group of 3 to 8 carbon atoms, preferably 3-6 carbon atoms derived from a saturated cyclic hydrocarbon. Cycloalkyl can be optionally substituted by $C_{1-3}$ alkyl groups or halogen. Usually, in the present case, cycloalkyl groups are cyclohexyl, methylcyclopropyl, cyclobutyl.

The term "halogen", as used herein, refers to an atom of chlorine, bromine, fluorine, iodine. Usually, in the present case, halogens are chlorine, fluorine, bromine.

The term "heterocycle" as used herein, refers to a 3 to 10 membered ring, containing at least one heteroatom selected form O or N or S or combinations of at least two thereof interrupting the carbocyclic ring structure. The heterocyclic ring can be saturated or non-saturated. The heterocyclic ring can be interrupted by a C=O, the S heteroatom can be oxidized. Heterocyclic ring moieties can optionally be substituted by hydroxyl, $C_{1-3}$ alkyl or halogen. Usually heterocyclic groups in the present case are piperidyl, pyrryl, furyl.

The term "aryl" as used herein, is defined as including an organic moiety derived from an aromatic hydrocarbon consisting of a ring containing 6 to 10 carbon atoms by removal of one hydrogen, which can optionally be substituted by 1 to 3 halogen atoms or by 1 to 2 $C_{1-3}$ alkyl groups. Usually aryl is phenyl.

The term "hydroxyl" as used herein, represents a group of formula "—OH".

The term "carbonyl" as used herein, represents a group of formula "—C=O".

The term "carboxyl" as used herein, represents a group of formula "—C(O)O—".

The term "cyano" as used herein, represents a group of formula "—CN".

The term "aldehyde" as used herein, represents a group of formula "—C(O)H".

The term "sulfonyl" as used herein, represents a group of formula "—$SO_2$".

The term "sulfate" as used herein, represents a group of formula "—O—S(O)$_2$—O—".

The term "carboxylic acid" as used herein, represents a group of formula "—C(O)OH".

The term "sulfoxide" as used herein, represents a group of formula "—S=O".

The term "phosphonic acid" as used herein, represents a group of formula "—P(O)(OH)$_2$".

The term "phosphoric acid" as used herein, represents a group of formula "—(O)P(O)(OH)$_2$".

The term "boronic acid", as used herein, represents a group of formula "—B(OH)$_2$".

The term "sulphonic acid" as used herein, represents a group of formula "—S(O)$_2$OH".

The term "modulator" as used herein, represents receptor agonist, antagonist, inverse agonist, inverse antagonist, partial agonist, partial antagonist.

Generally $R^1$ is hydrogen, halogen, $C_{1-6}$ alkyl. Usually R' is hydrogen.

Generally $R^2$ is $CR^3$ or N. Usually $R^2$ is $CR^3$.

Generally $R^3$ is hydrogen, halogen, O($C_{1-6}$ alkyl), S($C_{1-6}$ alkyl), cyano, aldehyde, heterocycle, $C_{1-6}$ alkyl or hydroxyl. Usually $R^3$ is hydrogen, $CF_3$, Br, Cl, OMe, Me, $OCHF_2$, $OCF_3$, SMe, furyl, —C(O)H, ethyl, cyano or n-propyl.

Generally $R^4$ is $CR^5$ or N.

Generally $R^5$ is hydrogen, halogen, non-substituted $C_{1-6}$ alkyl or hydroxyl. Usually $R^5$ is hydrogen, fluoro or methyl.

Generally $R^6$ is $CR^7$ or N.

Generally $R^7$ is —$NHR^{12}$, —S(O)$_2R^{14}$, —C(O)$NHR^{16}$, —$OR^{17}$, hydrogen, halogen, phosphonic acid, boronic acid, —$CH_2$—OH, —$CH_2$—S(O)$_2CH_3$, —(CH$_2$)$_a$—NH—(CH$_2$)$_b$—O$_c$—P(O)(OH)$_2$, —(CH$_2$)$_d$—C(NH$_2$)(CH$_2$OH)(CH$_2$—O—P(O)(OH)$_2$), —(CH$_2$)$_e$—C(NH$_2$)(CH$_3$)(CH$_2$—O—P(O)(OH)$_2$) or (CH$_2$)$_f$—NH—(CH$_2$)$_g$— SO$_3$H.

Usually $R^7$ is —NH—S(O)$_2CH_3$, hydrogen, —S(O)$_2NH_2$, hydroxyl, C(O)$NH_2$, $CH_2$OH, $CH_2$—S(O)$_2CH_3$, phosphonic acid or boronic acid.

Generally a is 1 or 2.
Generally b is 2 or 3.
Generally c is 0 or 1.
Generally d is 0 or 1.
Generally e is 0 or 1.
Generally f is 0 or 1.
Generally g is 2 or 3.
Generally $R^8$ is $CR^9$ or N.

Generally $R^9$ is hydrogen, halogen, non-substituted $C_{1-6}$ alkyl or phosphonic acid, boronic acid. Usually $R^9$ is hydrogen, fluoro or methyl.

Generally $R^{10}$ is $CR^{11}$ or N.

Generally $R^{11}$ is hydrogen, halogen or $C_{1-6}$ alkyl. Usually $R^{11}$ is hydrogen, chloro or methyl.

Generally $R^{12}$ is hydrogen, $C_{1-6}$ alkyl, —C(O)$R^{13}$, —S(O)$_2$($C_{1-3}$ alkyl), heterocycle. Usually $R^{12}$ is hydrogen, S(O)$_2$(methyl), —C(O)CH(NH$_2$)CH$_2$—COOH, C(O)CH$_3$, pyroyl or piperidinyl.

Generally $R^{13}$ is amino, $C_{1-6}$ alkyl. Usually $R^{13}$ is amino, methyl, —CH(NH$_2$)CH$_2$COOH.

Generally $R^{14}$ is $C_{1-4}$ alkyl, —$NHR^{15}$ or hydroxyl. Usually $R^{14}$ is amino, —NH(CH$_2$)$_2$COOH.

Generally $R^{15}$ is hydrogen, $C_{1-6}$ alkyl. Usually $R^{15}$ is H, methyl, —CH$_2$-heterocycle, —(CH$_2$)$_2$—COOH or —CH$_2$—P(O)(OH)$_2$.

Generally $R^{16}$ is hydrogen or $C_{1-6}$ alkyl. Usually $R^{16}$ is hydrogen.

Generally $R^{17}$ is hydrogen, $C_{1-6}$ alkyl or —S(O)$_2$($C_{1-3}$ alky). Usually $R^{17}$ is hydrogen, —S(O)$_2CH_3$.

Generally $R^{18}$ is $C_{2-4}$ alkyl or —O$C_{2-4}$ alkyl. Usually $R^{18}$ is methyl, n-propyl, O-ethyl or O-isopropyl.

Generally $R^{19}$ is hydrogen, halogen or $C_{1-6}$ alkyl. Usually $R^{19}$ is hydrogen.

Generally $R^{20}$ is hydrogen, halogen or $C_{1-6}$ alkyl. Usually $R^{20}$ is hydrogen.

Generally $R^{21}$ is —O$C_{1-4}$ alkyl. Usually $R^{21}$ is O-methyl or O-ethyl.

In one embodiment of the invention
$R^1$ is hydrogen; and
$R^2$ is $CR^3$; and
$R^3$ is halogen, O($C_{1-6}$ alkyl), S($C_{1-6}$ alkyl), cyano, aldehyde, heterocycle, $C_{1-6}$ alkyl; and
$R^4$ is $CR^5$ or N; and
$R^5$ is hydrogen or halogen; and
$R^6$ is $CR^7$ or N; and R⁷ is —NHR¹², —S(O)₂R¹⁴, —OR¹⁷, hydrogen, phosphonic acid, boronic acid, —CH₂—OH, —CH₂—S(O)₂CH₃; and R⁸ is CR⁹ or N; and
R⁹ is hydrogen, halogen or non-substituted $C_{1-6}$ alkyl; and
R¹⁰ is CR¹¹; and
R¹¹ is hydrogen, halogen or $C_{1-6}$ alkyl; and
R¹² is —S(O)₂($C_{1-3}$ alkyl), C(O)R¹³ or heterocycle; and
R¹³ is $C_{1-6}$ alkyl; and
R¹⁴ is NHR¹⁵; and
R¹⁵ is hydrogen or $C_{1-6}$ alkyl; and
R¹⁶ is $C_{1-6}$ alkyl; and
R¹⁷ is hydrogen, or —S(O)₂($C_{1-3}$ alkyl); and
R¹⁸ is $C_{2-4}$ alkyl or —$OC_{2-4}$ alkyl; and
R¹⁹ is hydrogen; and
R²⁰ is hydrogen; and
R²¹ is —$OC_{1-4}$ alkyl.

In another embodiment of the invention
R¹ is hydrogen; and
R² is CR³; and
R³ is halogen, O($C_{1-6}$ alkyl), $C_{1-6}$ alkyl; and
R⁴ is CR⁵ or N; and
R⁵ is hydrogen; and
R⁶ is CR⁷ or N; and
R⁷ is —NHR¹², —S(O)₂R¹⁴, —OR¹⁷, hydrogen, phosphonic acid or boronic acid; and
R⁸ is CR⁹; and
R⁹ is hydrogen; and
R¹⁰ is CR¹¹; and
R¹¹ is hydrogen or $C_{1-6}$ alkyl; and
R¹² is —S(O)₂($C_{1-3}$ alkyl) or C(O)R¹³; and
R¹³ is $C_{1-6}$ alkyl; and
R¹⁴ is NHR¹⁵; and
R¹⁵ is hydrogen; and
R¹⁷ is hydrogen; and
R¹⁸ is $C_{2-4}$ alkyl or —$OC_{2-4}$ alkyl; and
R¹⁹ is hydrogen; and
R²⁰ is hydrogen; and
R²¹ is —$OC_{1-4}$ alkyl.

Compounds of the invention are:
N-[4-(hydroxymethyl)phenyl]-7-methoxy-2-oxo-8-propyl-2H-chromene-3-carboxamide;
N-[4-(aminosulfonyl)-2-methylphenyl]-7-methoxy-2-oxo-8-propyl-2H-chromene-3-carboxamide;
N-[4-(aminosulfonyl)phenyl]-7-methoxy-2-oxo-8-propyl-2H-chromene-3-carboxamide;
N-[4-(aminosulfonyl)-2-bromophenyl]-7-methoxy-2-oxo-8-propyl-2H-chromene-3-carboxamide;
N-[4-(aminosulfonyl)-2-chlorophenyl]-7-methoxy-2-oxo-8-propyl-2H-chromene-3-carboxamide;
N-(4-amino-2-methylphenyl)-7-methoxy-2-oxo-8-propyl-2H-chromene-3-carboxamide;
7-methoxy-N-{2-methyl-4-[(methylsulfonyl)amino]phenyl}-2-oxo-8-propyl-2H-chromene-3-carboxamide;
N-{4-[(ethylsulfonyl)amino]-2-methylphenyl}-7-methoxy-2-oxo-8-propyl-2H-chromene-3-carboxamide;
N-[4-(acetylamino)-2-methylphenyl]-7-methoxy-2-oxo-8-propyl-2H-chromene-3-carboxamide;
7-methoxy-N-{2-methoxy-4-[(methylsulfonyl)amino]phenyl}-2-oxo-8-propyl-2H-chromene-3-carboxamide;
3-{[(4-{[(7-methoxy-2-oxo-8-propyl-2H-chromen-3-yl)carbonyl]amino}-3-methylphenyl)sulfonyl]amino}propanoic acid;
N-(2-chlorophenyl)-7-methoxy-2-oxo-8-propyl-2H-chromene-3-carboxamide;
7-methoxy-2-oxo-N-[4-(piperidin-3-ylamino)phenyl]-8-propyl-2H-chromene-3-carboxamide;
7-methoxy-2-oxo-8-propyl-N-[4-(pyrrolidin-3-ylamino)phenyl]-2H-chromene-3-carboxamide;
7-methoxy-2-oxo-N-{4-[(piperidin-2-ylmethyl)amino]phenyl}-8-propyl-2H-chromene-3-carboxamide;
7-methoxy-2-oxo-N-{4-[(piperidin-3-ylmethyl)amino]phenyl}-8-propyl-2H-chromene-3-carboxamide;
7-methoxy-N-(2-methylphenyl)-2-oxo-8-propyl-2H-chromene-3-carboxamide;
N-(2-cyanophenyl)-7-methoxy-2-oxo-8-propyl-2H-chromene-3-carboxamide;
7-methoxy-N-{4-[(methylsulfonyl)amino]-2-(trifluoromethyl)phenyl}-2-oxo-8-propyl-2H-chromene-3-carboxamide;
7-methoxy-N-{2-methyl-4-[(methylamino)sulfonyl]phenyl}-2-oxo-8-propyl-2H-chromene-3-carboxamide;
7-methoxy-N-[2-(methylthio)phenyl]-2-oxo-8-propyl-2H-chromene-3-carboxamide;
7-methoxy-2-oxo-8-propyl-N-[2-(trifluoromethoxy)phenyl]-2H-chromene-3-carboxamide;
N-[2-(2-furyl)phenyl]-7-methoxy-2-oxo-8-propyl-2H-chromene-3-carboxamide;
N-(3-fluoro-2-methylphenyl)-7-methoxy-2-oxo-8-propyl-2H-chromene-3-carboxamide;
N-(2-fluorophenyl)-7-methoxy-2-oxo-8-propyl-2H-chromene-3-carboxamide;
N-(2-chloropyridin-3-yl)-7-methoxy-2-oxo-8-propyl-2H-chromene-3-carboxamide;
N-(2-ethylphenyl)-7-methoxy-2-oxo-8-propyl-2H-chromene-3-carboxamide;
7-methoxy-N-(2-methoxyphenyl)-2-oxo-8-propyl-2H-chromene-3-carboxamide;
7-methoxy-2-oxo-8-propyl-N-[2-(trifluoromethyl)phenyl]-2H-chromene-3-carboxamide;
N-(2-bromophenyl)-7-methoxy-2-oxo-8-propyl-2H-chromene-3-carboxamide;
N-(4-hydroxy-2-methyl phenyl)-7-methoxy-2-oxo-8-propyl-2H-chromene-3-carboxamide;
4-{[(7-methoxy-2-oxo-8-propyl-2H-chromen-3-yl)carbonyl]amino}-3-methylphenyl methanesulfonate;
N-[2-(difluoromethoxy)phenyl]-7-methoxy-2-oxo-8-propyl-2H-chromene-3-carboxamide;
N-(3-bromopyridin-4-yl)-7-methoxy-2-oxo-8-propyl-2H-chromene-3-carboxamide;
N-(3-chloropyridin-4-yl)-7-methoxy-2-oxo-8-propyl-2H-chromene-3-carboxamide;
7-methoxy-N-(2-methoxypyridin-3-yl)-2-oxo-8-propyl-2H-chromene-3-carboxamide;
N-(2-chloro-5-methylpyridin-3-yl)-7-methoxy-2-oxo-8-propyl-2H-chromene-3-carboxamide;
N-(2-bromopyridin-3-yl)-7-methoxy-2-oxo-8-propyl-2H-chromene-3-carboxamide;
7-methoxy-2-oxo-8-propyl-N-(2-propylphenyl)-2H-chromene-3-carboxamide;
N-(6-amino-2-methylpyridin-3-yl)-7-methoxy-2-oxo-8-propyl-2H-chromene-3-carboxamide;
N-[4-(acetylamino)-2-(trifluoromethyl)phenyl]-7-methoxy-2-oxo-8-propyl-2H-chromene-3-carboxamide;
N-(2-ethylpyridin-3-yl)-7-methoxy-2-oxo-8-propyl-2H-chromene-3-carboxamide;
7-methoxy-N-{2-methyl-6-[(methylsulfonyl)amino]pyridin-3-yl}-2-oxo-8-propyl-2H-chromene-3-carboxamide;
7-methoxy-2-oxo-8-propyl-N-pyridin-4-yl-2H-chromene-3-carboxamide;
7-methoxy-N-(3-methylpyridin-4-yl)-2-oxo-8-propyl-2H-chromene-3-carboxamide;

7-methoxy-2-oxo-8-propyl-N-[3-(trifluoromethyl)pyridin-4-yl]-2H-chromene-3-carboxamide;
7-methoxy-2-oxo-8-propyl-N-pyridin-3-yl-2H-chromene-3-carboxamide;
N-[4-hydroxy-2-(trifluoromethyl)phenyl]-7-methoxy-2-oxo-8-propyl-2H-chromene-3-carboxamide;
7-methoxy-2-oxo-8-propyl-N-[2-(trifluoromethyl)pyridin-3-yl]-2H-chromene-3-carboxamide;
7-methoxy-N-(3-methylpyridin-2-yl)-2-oxo-8-propyl-2H-chromene-3-carboxamide;
7-methoxy-N-(2-methylpyridin-3-yl)-2-oxo-8-propyl-2H-chromene-3-carboxamide;
N-(2-formylpyridin-3-yl)-7-methoxy-2-oxo-8-propyl-2H-chromene-3-carboxamide;
N-(3-chloropyridazin-4-yl)-7-methoxy-2-oxo-8-propyl-2H-chromene-3-carboxamide;
(3-chloro-4-{[(7-methoxy-2-oxo-8-propyl-2H-chromen-3-yl)carbonyl]amino}phenyl)boronic acid;
N-(2-chloro-5-fluoropyridin-3-yl)-7-methoxy-2-oxo-8-propyl-2H-chromene-3-carboxamide;
(4-{[(7-methoxy-2-oxo-8-propyl-2H-chromen-3-yl)carbonyl]amino}-3-methylphenyl)phosphonic acid;
N-[4-(aminosulfonyl)-2-(trifluoromethyl)phenyl]-7-methoxy-2-oxo-8-propyl-2H-chromene-3-carboxamide;
(3S)-3-amino-4-[(4-{[(7-methoxy-2-oxo-8-propyl-2H-chromen-3-yl)carbonyl]amino}-3-methylphenyl)amino]-4-oxobutanoic acid;
8-isopropoxy-7-methoxy-2-oxo-N-[2-(trifluoromethyl)pyridin-3-yl]-2H-chromene-3-carboxamide;
8-isopropoxy-7-methoxy-N-(2-methylpyridin-3-yl)-2-oxo-2H-chromene-3-carboxamide;
8-ethoxy-7-methoxy-N-(2-methylpyridin-3-yl)-2-oxo-2H-chromene-3-carboxamide;
8-ethoxy-7-methoxy-2-oxo-N-[2-(trifluoromethyl)pyridin-3-yl]-2H-chromene-3-carboxamide;
8-ethoxy-7-methoxy-2-oxo-N-[2-(trifluoromethyl)phenyl]-2H-chromene-3-carboxamide;
8-isopropoxy-7-methoxy-2-oxo-N-[2-(trifluoromethyl)phenyl]-2H-chromene-3-carboxamide;
7-methoxy-N-{2-methyl-4-[(methylsulfonyl)methyl]phenyl}-2-oxo-8-propyl-2H-chromene-3-carboxamide;
N-{2-chloro-4-[(methylsulfonyl)amino]phenyl}-7-methoxy-2-oxo-8-propyl-2H-chromene-3-carboxamide;
(4R)-4-amino-5-[(4-{[(7-methoxy-2-oxo-8-propyl-2H-chromen-3-yl)carbonyl]amino}-3-methylphenyl)amino]-5-oxopentanoic acid;
N-[4-(aminosulfonyl)-2-methylphenyl]-7,8-diethoxy-2-oxo-2H-chromene-3-carboxamide;
N-[4-(aminosulfonyl)-2-methylphenyl]-8-ethoxy-7-methoxy-2-oxo-2H-chromene-3-carboxamide;
N-[4-(aminosulfonyl)-2-methylphenyl]-8-isopropoxy-7-methoxy-2-oxo-2H-chromene-3-carboxamide;
7,8-diethoxy-N-{4-[(methylsulfonyl)amino]-2-(trifluoromethyl)phenyl}-2-oxo-2H-chromene-3-carboxamide;
N-[4-(aminosulfonyl)-2-methylphenyl]-8-ethyl-7-methoxy-2-oxo-2H-chromene-3-carboxamide.

Preferred compounds of the invention are:
7-methoxy-2-oxo-8-propyl-N-[2-(trifluoromethyl)phenyl]-2H-chromene-3-carboxamide;
N-(3-bromopyridin-4-yl)-7-methoxy-2-oxo-8-propyl-2H-chromene-3-carboxamide;
N-(2-bromophenyl)-7-methoxy-2-oxo-8-propyl-2H-chromene-3-carboxamide;
7-methoxy-2-oxo-8-propyl-N-[3-(trifluoromethyl)pyridin-4-yl]-2H-chromene-3-carboxamide;
N-(3-chloropyridin-4-yl)-7-methoxy-2-oxo-8-propyl-2H-chromene-3-carboxamide;
8-ethoxy-7-methoxy-2-oxo-N-[2-(trifluoromethyl)pyridin-3-yl]-2H-chromene-3-carboxamide;
N-(2-ethylphenyl)-7-methoxy-2-oxo-8-propyl-2H-chromene-3-carboxamide;
(4-{[(7-methoxy-2-oxo-8-propyl-2H-chromen-3-yl)carbonyl]amino}-3-methylphenyl)phosphonic acid;
(3-chloro-4-{[(7-methoxy-2-oxo-8-propyl-2H-chromen-3-yl)carbonyl]amino}phenyl)boronic acid;
7-methoxy-2-oxo-8-propyl-N-[2-(trifluoromethoxy)phenyl]-2H-chromene-3-carboxamide;
N-[2-(difluoromethoxy)phenyl]-7-methoxy-2-oxo-8-propyl-2H-chromene-3-carboxamide;
N-[4-(aminosulfonyl)-2-methylphenyl]-8-isopropoxy-7-methoxy-2-oxo-2H-chromene-3-carboxamide;
N-[4-(aminosulfonyl)-2-methylphenyl]-8-ethoxy-7-methoxy-2-oxo-2H-chromene-3-carboxamide;
N-[4-(aminosulfonyl)phenyl]-7-methoxy-2-oxo-8-propyl-2H-chromene-3-carboxamide;
N-[4-(acetylamino)-2-methylphenyl]-7-methoxy-2-oxo-8-propyl-2H-chromene-3-carboxamide;
7-methoxy-2-oxo-8-propyl-N-[2-(trifluoromethyl)pyridin-3-yl]-2H-chromene-3-carboxamide;
N-(2-bromopyridin-3-yl)-7-methoxy-2-oxo-8-propyl-2H-chromene-3-carboxamide;
N-(2-ethylpyridin-3-yl)-7-methoxy-2-oxo-8-propyl-2H-chromene-3-carboxamide;
7-methoxy-N-(2-methylpyridin-3-yl)-2-oxo-8-propyl-2H-chromene-3-carboxamide;
7-methoxy-N-{4-[(methylsulfonyl)amino]-2-(trifluoromethyl)phenyl}-2-oxo-8-propyl-2H-chromene-3-carboxamide;
7,8-diethoxy-N-{4-[(methylsulfonyl)amino]-2-(trifluoromethyl)phenyl}-2-oxo-2H-chromene-3-carboxamide;
N-[4-(aminosulfonyl)-2-bromophenyl]-7-methoxy-2-oxo-8-propyl-2H-chromene-3-carboxamide;
N-[4-(aminosulfonyl)-2-chlorophenyl]-7-methoxy-2-oxo-8-propyl-2H-chromene-3-carboxamide;
7-methoxy-N-{2-methyl-4-[(methylsulfonyl)amino]phenyl}-2-oxo-8-propyl-2H-chromene-3-carboxamide;
7-methoxy-N-{2-methyl-6-[(methylsulfonyl)amino]pyridin-3-yl}-2-oxo-8-propyl-2H-chromene-3-carboxamide;
7-methoxy-N-{2-methoxy-4-[(methylsulfonyl)amino]phenyl}-2-oxo-8-propyl-2H-chromene-3-carboxamide;
N-[4-(aminosulfonyl)-2-methylphenyl]-7,8-diethoxy-2-oxo-2H-chromene-3-carboxamide;
7-methoxy-N-(2-methoxypyridin-3-yl)-2-oxo-8-propyl-2H-chromene-3-carboxamide;
N-{4-[(ethylsulfonyl)amino]-2-methylphenyl}-7-methoxy-2-oxo-8-propyl-2H-chromene-3-carboxamide;
N-[4-(acetylamino)-2-(trifluoromethyl)phenyl]-7-methoxy-2-oxo-8-propyl-2H-chromene-3-carboxamide;
N-(4-hydroxy-2-methyl phenyl)-7-methoxy-2-oxo-8-propyl-2H-chromene-3-carboxamide;
(3S)-3-amino-4-[(4-{[(7-methoxy-2-oxo-8-propyl-2H-chromen-3-yl)carbonyl]amino}-3-methylphenyl)amino]-4-oxobutanoic acid;
N-(2-chloropyridin-3-yl)-7-methoxy-2-oxo-8-propyl-2H-chromene-3-carboxamide;
(4R)-4-amino-5-[(4-{[(7-methoxy-2-oxo-8-propyl-2H-chromen-3-yl)carbonyl]amino}-3-methylphenyl)amino]-5-oxopentanoic acid;
N-[4-(aminosulfonyl)-2-methylphenyl]-7-methoxy-2-oxo-8-propyl-2H-chromene-3-carboxamide;
N-[4-hydroxy-2-(trifluoromethyl)phenyl]-7-methoxy-2-oxo-8-propyl-2H-chromene-3-carboxamide.

Most preferred compounds of the invention are:

7-methoxy-2-oxo-8-propyl-N-[2-(trifluoromethyl)pyridin-3-yl]-2H-chromene-3-carboxamide;
N-(2-bromopyridin-3-yl)-7-methoxy-2-oxo-8-propyl-2H-chromene-3-carboxamide;
N-(2-ethylpyridin-3-yl)-7-methoxy-2-oxo-8-propyl-2H-chromene-3-carboxamide;
7-methoxy-N-(2-methylpyridin-3-yl)-2-oxo-8-propyl-2H-chromene-3-carboxamide;
7-methoxy-N-{4-[(methylsulfonyl)amino]-2-(trifluoromethyl)phenyl}-2-oxo-8-propyl-2H-chromene-3-carboxamide;
7,8-diethoxy-N-{4-[(methylsulfonyl)amino]-2-(trifluoromethyl)phenyl}-2-oxo-2H-chromene-3-carboxamide;
N-[4-(aminosulfonyl)-2-bromophenyl]-7-methoxy-2-oxo-8-propyl-2H-chromene-3-carboxamide;
N-[4-(aminosulfonyl)-2-chlorophenyl]-7-methoxy-2-oxo-8-propyl-2H-chromene-3-carboxamide;
7-methoxy-N-{2-methyl-4-[(methylsulfonyl)amino]phenyl}-2-oxo-8-propyl-2H-chromene-3-carboxamide;
7-methoxy-N-{2-methyl-6-[(methylsulfonyl)amino]pyridin-3-yl}-2-oxo-8-propyl-2H-chromene-3-carboxamide;
7-methoxy-N-{2-methoxy-4-[(methylsulfonyl)amino]phenyl}-2-oxo-8-propyl-2H-chromene-3-carboxamide;
N-[4-(aminosulfonyl)-2-methylphenyl]-7,8-diethoxy-2-oxo-2H-chromene-3-carboxamide;
7-methoxy-N-(2-methoxypyridin-3-yl)-2-oxo-8-propyl-2H-chromene-3-carboxamide;
N-{4-[(ethylsulfonyl)amino]-2-methylphenyl}-7-methoxy-2-oxo-8-propyl-2H-chromene-3-carboxamide;
N-[4-(acetylamino)-2-(trifluoromethyl)phenyl]-7-methoxy-2-oxo-8-propyl-2H-chromene-3-carboxamide;
N-(4-hydroxy-2-methyl phenyl)-7-methoxy-2-oxo-8-propyl-2H-chromene-3-carboxamide;
(3S)-3-amino-4-[(4-{[(7-methoxy-2-oxo-8-propyl-2H-chromen-3-yl)carbonyl]amino}-3-methylphenyl)amino]-4-oxobutanoic acid;
N-(2-chloropyridin-3-yl)-7-methoxy-2-oxo-8-propyl-2H-chromene-3-carboxamide;
(4R)-4-amino-5-[(4-{[(7-methoxy-2-oxo-8-propyl-2H-chromen-3-yl)carbonyl]amino}-3-methylphenyl)amino]-5-oxopentanoic acid;
N-[4-(aminosulfonyl)-2-methylphenyl]-7-methoxy-2-oxo-8-propyl-2H-chromene-3-carboxamide;
N-[4-hydroxy-2-(trifluoromethyl)phenyl]-7-methoxy-2-oxo-8-propyl-2H-chromene-3-carboxamide.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic, for example, a hydrohalic such as hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahl & Camille G. Wermuth (Eds), Verlag Helvetica Chimica Acta Zurich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the sphingosine-1-phosphate receptors.

In another embodiment, there are provided pharmaceutical compositions including at least one compound of the invention in a pharmaceutically acceptable carrier.

In a further embodiment of the invention, there are provided methods for treating disorders associated with modulation of sphingosine-1-phosphate receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by S1P1 modulation: not limited to the treatment of diabetic retinopathy, other retinal degenerative conditions, dry eye, angiogenesis and wounds.

Therapeutic utilities of S1P1 agonists are ocular disease, such as but not limited to: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases such as but not limited to: various inflammatory diseases, including acute lung injury, its prevention, sepsis, tumor metastasis, atherosclerosis, pulmonary edemas, and ventilation-induced lung injury; or autoimmune diseases and immunosuppression such as but not limited to: rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermatitis, and organ transplantation; or allergies and other inflammatory diseases such as but not limited to: urticaria, bronchial asthma, and other airway inflammations including pulmonary emphysema and chronic obstructive pulmonary diseases; or cardiac protection such as but not limited to: ischemia reperfusion injury and atherosclerosis; or wound healing such as but not limited to: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation such as but not limited to: treatment of osteoporosis and various bone fractures including hip and ankles; or anti-nociceptive activity such as but not limited to: visceral pain, pain associated with diabetic neuropathy, rheumatoid arthritis, chronic knee and joint pain, tendonitis, osteoarthritis, neuropathic pains.

In still another embodiment of the invention, there are provided methods for treating disorders associated with modulation of sphingosine-1-phosphate receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular disease, wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases, various inflammatory diseases, including acute lung injury, its prevention, sepsis, tumor metastasis, atherosclerosis, pulmonary edemas, and ventilation-induced lung injury; or autoimmune diseases and immunosuppression, rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermatitis, and organ transplantation; or allergies and other inflammatory diseases, urticaria, bronchial asthma, and other airway inflammations including pulmonary emphysema and chronic obstructive pulmonary diseases; or cardiac protection, ischemia reperfusion injury and atherosclerosis; or wound healing, scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation, treatment of osteoporosis and various bone fractures including hip and ankles; or anti-nociceptive activity, visceral pain, pain associated with diabetic neuropathy, rheumatoid arthritis, chronic knee and joint pain, tendonitis, osteoarthritis, neuropathic pains.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier therefor. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3- butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and or alleviations of conditions which are responsive to treatment by agonists or functional antagonists of sphingosine-1-phosphate receptors. Thus, in further embodiments of the invention, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I.

The compounds of formula I according to the invention can be prepared analogously to conventional methods as understood by the person skilled in the art of synthetic organic chemistry.

The synthetic scheme set forth below, illustrates how compounds according to the invention can be made. Those skilled in the art will be able to routinely modify and/or adapt the following scheme to synthesize any compounds of the invention covered by Formula I.

General schemes for synthesizing coumarin derivatives:

Method A

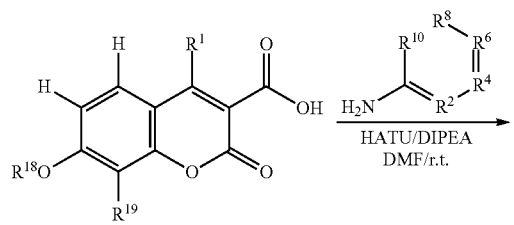

-continued

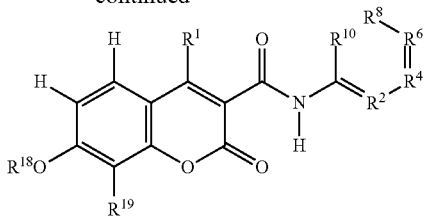

Substituted 2H-chromene-3-carboxylic acids intermediates, prepared from known procedures, and the desired aniline in N,N-dimethylformamide were treated with o-(7-azabenzotriazole-1-yl)-N,N,N',N'-tetramethyluronium hexafluorophosphate and diisopropylethyl amine. The reaction was stirred at room temperature for 16 hours. The solution was quenched with water and the product extracted with ethylacetate. The organic layers were combined and dried over sodium sulfate. The organic layer was filtered and evaporated under vacuum to afford the crude amide. Purification via medium pressure liquid chromatography (gradient MeOH/DCM) afforded the desired compound the corresponding compound of Formula I.

Method B

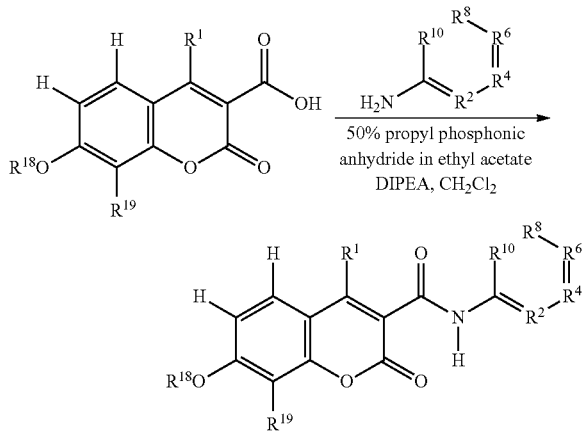

To the substituted-2H-chromene-3-carboxylic acids intermediates, prepared from known procedures, in dichloromethane are added diisopropyl ethyl amine and a 50% solution of propylphosphonic anhydride in ethyl acetate. The mixture was stirred for 30 minutes at room temperature. The desired aniline is added to the reaction mixture which is stirred at room temperature overnight. The reaction mixture is then poured onto ice water and dichloromethane is added. The organic layer is separated and washed with brine dried with sodium sulfate, filtered and concentrated to dryness. The residue was triturated with dichloromethane/Hexanes and then the solid was passed through a medium pressure liquid chromatography to give the corresponding compound of Formula I.

BRIEF DESCRIPTION OF THE DRAWINGS

FIG. 1 shows lymphopenia induced by S1P1 agonists (10 mg/kg) in mice.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of protium $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diastereoisomeric isomers, chromatographic separation may be employed.

The IUPAC names of the compounds mentioned in the examples were generated with ACD version 8.

Unless specified otherwise in the examples, characterization of the compounds is performed according to the following methods:

NMR spectra are recorded on 300 or 600 MHz Varian and acquired at room temperature. Chemical shifts are given in ppm referenced either to internal trimethylsilyl or to the residual solvent signal.

All the reagents, solvents, catalysts for which the synthesis is not described are purchased from chemical vendors such as Sigma Aldrich, Fluke, Bio-Blocks, Ryan Scientific, Syn Chem, Chem-Impex, Aces Pharma, however some known intermediates, for which the CAS registry number [CAS #] are mentioned, were prepared in-house following known procedures.

Usually the compounds of the invention were purified by flash column chromatography using a gradient solvent system of methanol/dichloromethane unless otherwise reported.

The following abbreviations are used in the examples:
NH$_3$ ammonia
BOC tert-butyloxy carbonyl
CH$_3$CN acetonitrile
PPPA propylphosphonic anhydride
PSI pound per square inch
ClSO$_2$OH chlorosulfonic add
DIPEA diisopropylethyl amine
DCM dichloromethane
DMF N,N-dimethylformamide
HATU o-(7-azabenzotriazole-1-yl)-N,N,N',N'-tetramethyluronium hexafluorophosphate
NaOH sodium hydroxide
MeOH methanol
CD$_3$OD deuterated methanol
NH$_3$ ammonia
HCl hydrochloric acid
NaIO$_4$ sodium periodate
Na$_2$SO$_4$ sodium sulfate
ON overnight
R.T. room temperature
MgSO$_4$ magnesium sulfate
EtOAc ethyl acetate
CDCl$_3$ deuterated chloroform
DMSO-d$_6$ deuterated dimethyl sulfoxide
MPLC medium pressure liquid chromatography
TFA trifluoroacetic acid
THF tetrahydrofuran
PdCl$_2$(PPh$_3$)$_2$ bis(triphenylphosphine)palladium(II) chloride
LiCl lithium chloride
Pd(PPh$_3$)$_4$ tetrakis(triphenylphosphine) palladium
CH$_3$CN acetonitrile
TEA triethylamine
EDTA ethylenediaminetetraacetic acid
BCl$_3$ boron trichloride
NaHCO$_3$ sodium bicarbonate
TBME tert-butyl methylether
CH$_3$CHO acetaldehyde
Hantzsch ester diethyl 1,4-dihydro-2,6-dimethyl-3,5-pyridinedicarboxylate The following synthetic schemes illustrate how compounds according to the invention can be made. Those skilled in the art will be routinely able to modify and/or adapt the following schemes to synthesize any compound of the invention covered by Formula I.

Some compounds of this invention can generally be prepared in one step from commercially available literature starting materials.

Example 1

Compound 1

N-(3-Fluoro-2-methylphenyl)-7-methoxy-2-oxo-8-propyl-2H-chromene-3-carboxamide

7-Methoxy-2-oxo-8-propyl-2H-chromene-3-carboxylic acid (CAS 952504-50-6) (Intermediate 1) (0.20 g, 0.76 mmol) and 3-fluoro-2-methyl-phenylamine [CAS 443-86-7] (0.09 mL, 0.84 mmol) in DMF (20 mL) were treated with HATU (0.42 g, 1.1 mmol) and diisopropylethyl amine (0.38 mL, 2.3 mmol). The reaction was stirred at r.t. for 16 hours. The solution was quenched with water and the product extracted with EtOAc. The organic layers were combined and dried over Na$_2$SO$_4$. The organic layer was filtered and evaporated under vacuum to afford the crude title compound. Purification via MPLC (gradient MeOH/DCM) afforded 0.14 g (50%) of Compound 1.

$^1$H NMR (600 MHz, CDCl$_3$-d$_3$) δ 10.92 (s, 1H), 8.95 (s, 1H), 8.11 (d, J=8.2 Hz, 1H), 7.58 (d, J=8.7 Hz, 1H), 7.25-7.17 (m, 1H), 6.98 (d, J=8.8 Hz, 1H), 6.87 (t, J=8.7 Hz, 1H), 3.98 (s, 3H), 2.93-2.78 (m, 2H), 2.34 (d, J=1.3 Hz, 3H), 1.67-1.60 (m, 2H), 1.00 (t, J=7.3 Hz, 3H).

Example 2

Intermediate 2

8-Ethyl-7-methoxy-2-oxo-2H-chromene-3-carboxylic acid

Step 1: 1,3-Cyclohexanedione (10 g, 89.2 mmol), 40% aqueous CH$_3$CHO (49.4 g, 445.9 mmol) were dissolved in methanol (40 mL) followed by addition of Hantzsch ester (22.7 g, 89.2 mmol) and pyridine (2.1 g, 18.74 mmol) under nitrogen. The resulting light yellow mixture was stirred at room temperature overnight, then concentrated to give crude product that was re-slurried in a mixture of CH$_2$Cl$_2$ (40 mL) and hexanes (60 mL) to furnish 2-ethyl-1,3-cyclohexanedione (8.6 g, 69%).

Step 2: 2-Ethyl-1,3-cyclohexanedione (15 g, 107 mmol), mesitylene (240 mL), and 5% Pd/C (7.8 g) were placed in a flask. The reaction mixture was stirred at 160° C. for two days. Filtration gave a crude product, which was purified by chromatography (EtOAc/Hexane) to give 2-ethyl-3-hydroxy phenol (2.2 g, 15%).

Step 3: DMF (46 mL) was placed in a flask followed by addition of POCl$_3$ (30.2 g, 194.34 mmol) dropwise at 0° C. The mixture was stirred at −5° C. for 30 min followed by addition of a solution of 2-ethyl-3-hydroxy phenol (8.95 g, 64.78 mmol) in DMF (40 mL). After 3.5 hours, the reaction mixture was poured into 2M aq. NaOH, and extracted with EtOAc (2×200 mL). The remained aqueous solution was neutralized with 5M aq. HCl. to pH ~5, extracted with EtOAc (2×200 mL), and the EtOAc phase was dried over Na$_2$SO$_4$, concentrated, purified by chromatography (EtOAc/Hexane) to give a desired product (11 g, 62%).

Step 4: Sodium hydride (60%, 2.8 g) was added portionwise to a solution of 2-ethyl-3,4-dihydroxybenzaldehyde (5.8 g, 34.93 mmol) in DMSO (80 mL) at −10° C. under nitrogen, and the resulting mixture was stirred at −10° C. for 1.5 hours followed by addition of iodomethane (4.96 g, 34.93 mmol) dropwise. The solution was warmed to room temperature, and stirred overnight. The reaction solution was poured into ice/water, extracted with TBME. The combined organic phase was dried over anhydrous Na$_2$SO$_4$, and concentrated to give a crude product that was purified by chromatography to give 2-hydroxy-4-methoxy-3-ethyl-benzaldehyde (3.75 g, 55%).

Step 5: To a solution of 2-hydroxy-4-methoxy-3-ethyl-benzaldehyde (3.1 g, 17.2 mmol) in ethanol (93 mL) is added diethyl malonate (2.8 g, 17.2 mmol) and piperidine (1.5 g, 17.2 mmol). The reaction mixture was stirred at room temperature overnight. The reaction mixture was then cooled to 0° C. with ice/water bath and the formed precipitate was filtered and washed with ethanol to give 7-methoxy-2-oxo-8-ethyl-2H-chromene-3-carboxylic acid ethyl ester (3.1 g, 65%).

Step 6: To a solution of 7-methoxy-2-oxo-8-ethyl-2H-chromene-3-carboxylic acid ethyl ester (3.1 g, 11.2 mmol) in THF (62 mL) was added at 0° C. a 1M solution of NaOH (25 mL). The reaction mixture was stirred at room temperature overnight. The mixture was cooled to 0° C. with ice/water bath and pH was adjusted to ~1 by adding 1M HCl solution. The formed precipitate was filtered and washed with water, dried to give the title Intermediate 2 (2.55 g, 99%).

$^1$H NMR (300 MHz, DMSO-d$_6$) δ 12.95 (br s, 1H), 8.69 (s, 1H), 7.77 (d, J=8.8 Hz, 1H), 7.13 (d, J=8.8 Hz, 1H), 3.93 (s, 3H), 2.71 (q, J=7.3 Hz, 2H), 1.08 (t, J=7.3 Hz, 3H).

Example 3

Intermediate 3

7,8-Diethoxy-2-oxo-2H-chromene-3-carboxylic acid

Step 1: Sodium hydride (60%, 64 g) was added portionwise to a solution of 2,3,4-trihydroxybenzaldehyde (61.6 g, 400 mmol) at −10° C. under nitrogen, and the resulting mixture was stirred at −10° C. for 1.5 hours followed by addition of iodoethane (206 g, 1.32 mol) dropwise. The solution was warmed to room temperature, and stirred overnight. The reaction solution was poured into ice/water (3.5 kg), extracted with TBME (500 mL×5). The combined organic phase was washed with sat. NaHCO$_3$ (400 mL×3) and water (400 mL×2), dried over anhydrous Na$_2$SO$_4$, and concentrated to give a crude product (50 g) that was used directly for the next step without further purification.

Step 2: A solution of crude 2,3,4-triethoxybenzaldehyde (50 g) from step 1 was dissolved in CH$_2$Cl$_2$ followed by slow addition of 1M BCl$_3$ in CH$_2$Cl$_2$ (188 mL) while controlling the temperature at about 25° C. The resulting mixture was stirred at room temperature for 2 hours and then carefully poured into sat. aq. NaHCO$_3$. The solution was adjusted to pH ~1 by addition of concentrated HCl. The organic phase was separated, and the aqueous phase was extracted with TBME. The combined organic phase was dried over anhydrous Na$_2$SO$_4$, concentrated to give a crude product that was purified by chromatography to furnish the desired product (9.8 g, 21%).

Step 3: The material from Step 2 (11.2 g, 53.3 mmol) and diethyl malonate (8.54 g, 53.3 mmol) were dissolved in anhydrous ethanol (310 mL) under nitrogen. The mixture was cooled with ice/water followed by addition of piperidine (4.54 g, 53.3 mmol), and stirred at room temperature for 2 hours. The reaction solution was stored at −20° C. for 3 hours. Filtration gave a crude solid that was washed with cooled ethanol, and then dissolved in CH$_2$Cl$_2$, dried over anhydrous Na$_2$SO$_4$, concentrated to give a crude product that was purified by chromatography (EtOAc/Hexane) to obtain a desired product (14.0 g, 85.9%).

Step 4: The material from Step 3 (14.0 g, 45.7 mmol) was dissolved in THF (280 mL), cooled with ice/water followed by addition of 1M aq. NaOH (220 mL), and stirred at room temperature overnight. The organic phase was separated, and the aqueous phase was extracted with TBME (100 mL×3). The aqueous phase was adjusted to pH ~1 by 1M aq. HCl, and then added CH$_2$Cl$_2$. The CH$_2$Cl$_2$ phase was separated and the aqueous phase was extracted with CH$_2$Cl$_2$. The combined CH$_2$Cl$_2$ was dried over anhydrous Na$_2$SO$_4$, and concentrated to give a light yellow solid as the title compound (12 g, 94.5%).

$^1$H NMR (300 MHz, DMSO-d$_6$) δ 12.98 (s, 1H), 8.66 (s, 1H), 7.61 (d, J=9.0 Hz, 1H), 7.15 (d, J=8.8 Hz, 1H), 4.20 (q, J=7.0 Hz, 2H), 4.07 (q, J=7.0 Hz, 2H), 1.37 (t, J=6.9 Hz, 3H), 1.28 (t, J=7.0 Hz, 3H).

Example 4

Intermediate 4

8-Isopropoxy-7-methoxy-2-oxo-2H-chromene-3-carboxylic acid

Step 1: A solution of 2,3,4-trimethoxybenzaldehyde (9.81 g, 50 mmol) was dissolved in CH$_2$Cl$_2$ (250 mL) followed by addition of BCl$_3$ solution (1M, in CH$_2$Cl$_2$, 50 mL) dropwise.

The mixture was stirred at room temperature for 2 hours, and then added another equivalent of BCl$_3$ solution (1M in CH$_2$Cl$_2$, 50 mL). The reaction mixture was stirred at RT overnight, and poured into 10% NaHCO$_3$. The aqueous layer was acidified by 2M H$_2$SO$_4$ to pH ~1, extracted with EtOAc, dried over Na$_2$SO$_4$, concentrated to give a grey product (7.4 g, 88%).

Step 2: The compound from the previous step (20 g, 118.94 mmol) was added to a solution of sodium hydride (60%, 11 g) in dry DMSO (300 mL). The mixture was stirred for 40 min, added potassium iodide (20.0 g, 120.5 mmol) and stirred another 10 minutes followed by addition of 2-bromopropane (15.0 g, 122 mmol). The mixture was stirred overnight, diluted with EtOAc. The organic phase was dried over Na$_2$SO$_4$ and concentrated to give a crude product that was purified by chromatography (EtOAc/Hexane) to give a desired product (5.4 g, 21%).

Step 3: The compound from the previous step (10.8 g, 51.37 mmol) and diethyl malonate (8.9 g, 55.57 mmol) were dissolved in anhydrous ethanol (300 mL) under nitrogen. The mixture was cooled with ice/water followed by addition of piperidine (4.7 g, 55.20 mmol), and stirred at room temperature for 2 hours. The reaction solution was stored at −20° C. for 3 hours. Filtration gave a crude solid that was washed with cooled ethanol, dried to obtain a desired product (10.4 g, 65%).

Step 4: The material from the previous step (8.3 g, 27.1 mmol) was dissolved in THF (100 mL), cooled with ice/water followed by addition of 1M aq. NaOH (50 mL), and stirred at room temperature overnight. The organic phase was separated, and the aqueous phase was extracted with TBME (50 mL×2). The remained aqueous phase was adjusted to pH ~1 by 1M aq. HCl, and then cooled to 0° C. Filtration and drying gave a light yellow title intermediate (7 g, 25.16 mmol, 93.2%).

$^1$H NMR (300 MHz, DMSO-d$_6$) δ 12.98 (br s, 1H), 8.68 (s, 1H), 7.63 (d, J=8.8 Hz, 1H), 7.17 (d, J=8.8 Hz, 1H), 4.50-4.34 (m, 1H), 3.91 (s, 3H), 1.24 (d, J=6.2 Hz, 6H).

Example 5

Intermediate 5

8-Ethoxy-7-methoxy-2-oxo-2H-chromene-3-carboxylic acid

Step 1: A solution of 2,3,4-trimethoxybenzaldehyde (9.81 g, 50 mmol) was dissolved in CH$_2$Cl$_2$ (250 mL) followed by addition of BCl$_3$ solution (1M, in CH$_2$Cl$_2$, 50 mL) dropwise. The mixture was stirred at room temperature for 2 hours, and then added another equivalent of BCl$_3$ solution (1M in CH$_2$Cl$_2$, 50 mL). The reaction mixture was stirred at room temperature overnight, and poured into 10% NaHCO$_3$. The aqueous layer was acidified by 2M H$_2$SO$_4$ to pH ~1, extracted with EtOAc, dried over Na$_2$SO$_4$, concentrated to give a grey product (7.4 g, 88%).

Step 2: The product from the previous step (10.0 g, 59.47 mmol) was added to a solution of sodium hydride (4.8 g, 60%, 120 mmol) in dry DMSO (200 mL). The mixture was stirred for 20 min and iodoethane (9.4 g, 60.27 mmol) was added then stirred overnight. The reaction was quenched with water, adjusted by con. HCl to pH ~6, extracted with EtOAc. The organic phase was washed with H$_2$O and sat. aq. NaCl, dried, and concentrated to give a brown oil product (12 g, 55%).

Step 3: The product from the previous step (10.8 g, 55 mmol) and diethyl malonate (8.9 g, 55.6 mmol) were dissolved in anhydrous ethanol (300 mL) under nitrogen. The mixture was cooled with ice/water followed by addition of piperidine (4.7 g, 55.2 mmol), and stirred at room temperature for 2 hours. The reaction solution was stored at −20° C. for 3 hours. Filtration gave a crude solid that was washed with cooled ethanol, dried to obtain a desired product (10.4 g, 35.6 mmol, 65%).

Step 4: The product from the previous step (15.0 g, 51.32 mmol) was dissolved in THF (300 mL), cooled with ice/water followed by addition of 1M aq. NaOH (150 mL), and stirred at room temperature overnight. The organic phase was separated, and the aqueous phase was extracted with TBME (100 mL×3). The remained aqueous phase was adjusted to pH ~1 by 1M aq. HCl, and cooled to 0° C. Filtration and drying gave a light yellow title compound (13.2 g, 49.96 mmol, 97.5%).

$^1$H NMR (300 MHz, DMSO-d$_6$) δ 13.00 (br s, 1H), 8.68 (s, 1H), 7.64 (d, J=8.8 Hz, 1H), 7.17 (d, J=9.1 Hz, 1H), 4.06 (q, J=7.0 Hz, 2H), 3.92 (s, 3H), 1.28 (t, J=7.0 Hz, 3H).

Compounds 2-16, 18-20, 22-24, 26-40, 43-45, 47, 48, 51, 54, 56, 57, 58, 59, 60, 61, 64, 65, 62, 63, 69, 70, 71 and 72 were prepared from Intermediate 1 (unless otherwise specified) and the corresponding amine, in a similar manner to the method described in Example 1 for Compound 1. The reagents used and the results are described below in Table 1.

TABLE 1

| Compound number | IUPAC name | Reagent(s) used | $^1$H NMR δ (ppm) for Compound |
|---|---|---|---|
| 2 | N-(2-fluorophenyl)-7-methoxy-2-oxo-8-propyl-2H-chromene-3-carboxamide | 2-fluorophenylamine [CAS 348-54-9] | (600 MHz; CDCl$_3$) δ 11.18 (br s, 1H), 8.92 (s, 1H), 8.50 (td, J = 1.5, 8.0 Hz, 1H), 7.57 (d, J = 8.7 Hz, 1H), 7.20-7.13 (m, 2H), 7.12-7.08 (m, 1H), 6.97 (d, J = 8.8 Hz, 1H), 3.98 (s, 3H), 2.87 (dd, J = 7.0, 8.4 Hz, 2H), 1.63 (s × t, J = 7.5 Hz, 2H), 1.00 (t, J = 7.3 Hz, 3H). |
| 3 | N-(2-chloropyridin-3-yl)-7-methoxy-2-oxo-8-propyl-2H-chromene-3-carboxamide | 2-chloro-pyridin-3-ylamine [CAS 6298-19-7] | (600 MHz, CDCl$_3$) δ 11.53 (br s, 1H), 9.00-8.88 (m, 1H), 8.16 (br s, 1H), 7.82 (br. s., 1H), 7.59 (d, J = 8.6 Hz, 1H), 7.38-7.24 (m, 1H), 7.06 (br. s., 3H), 6.99 (d, J = 8.5 Hz, 1H), 3.99 (s, 2 H), 2.87 (t, J = 7.6 Hz, 1H), 1.74-1.50 (m, 1H), 1.00 (t, J = 7.3 Hz, 3H). |
| 4 | 7-methoxy-2-oxo-8-propyl-N-[2- | 2-trifluoromethyl-phenylamine [CAS 88-17-5] | (600 MHz, CDCl$_3$) δ 11.25 (s, 1H), 8.93 (s, 1H), 8.41 (d, J = 8.4 Hz, 1H), 7.68 (d, J = 7.8 Hz, 1H), |

TABLE 1-continued

| Compound number | IUPAC name | Reagent(s) used | $^1$H NMR δ (ppm) for Compound |
|---|---|---|---|
| | (trifluoromethyl)phenyl]-2H-chromene-3-carboxamide | | 7.60 (t, J = 7.9 Hz, 1H), 7.57 (d, J = 8.7 Hz, 1H), 7.27 (t, J = 7.6 Hz, 1H), 6.97 (d, J = 8.7 Hz, 1H), 3.98 (s, 3H), 2.86 (dd, J = 6.9, 8.5 Hz, 2H), 1.62 (s × t, J = 7.5 Hz, 2H), 1.00 (t, J = 7.3 Hz, 3H). |
| 5 | N-(2-bromophenyl)-7-methoxy-2-oxo-8-propyl-2H-chromene-3-carboxamide | 2-bromo-phenylamine [CAS 615-36-1] | (600 MHz, CDCl$_3$) δ 11.32 (s, 1H), 8.94 (s, 1H), 8.57 (dd, J = 1.5, 8.4 Hz, 1H), 7.61 (dd, J = 1.4, 8.0 Hz, 1H), 7.58 (d, J = 8.7 Hz, 1H), 7.38-7.34 (m, 1H), 7.02 (td, J = 1.5, 7.7 Hz, 1H), 6.97 (d, J = 8.7 Hz, 1H), 3.98 (s, 3H), 2.86 (dd, J = 6.9, 8.5 Hz, 2H), 1.68-1.59 (m, 2H), 1.00 (t, J = 7.3 Hz, 3H). |
| 6 | N-(3-bromopyridin-4-yl)-7-methoxy-2-oxo-8-propyl-2H-chromene-3-carboxamide | 3-bromo-pyridin-4-ylamine [CAS 13534-98-0] | (600 MHz, CDCl$_3$) δ 11.65 (br s, 1H), 8.94 (s, 1H), 8.73 (br s, 1H), 8.61 (br s, 1H), 8.49 (br s, 1H), 7.61 (d, J = 8.7 Hz, 1H), 7.00 (d, J = 8.8 Hz, 1H), 4.00 (s, 3H), 2.87 (t, J = 7.6 Hz, 2H), 1.69-1.56 (m, 2H), 1.00 (t, J = 7.3 Hz, 3H). |
| 7 | 7-methoxy-2-oxo-8-propyl-N-pyridin-4-yl-2H-chromene-3-carboxamide | pyridin-4-ylamine [CAS 504-24-5] | (600 MHz, CDCl$_3$) δ 11.08 (s, 1H), 8.92 (s, 1H), 8.56 (d, J = 5.1 Hz, 2H), 7.67 (d, J = 6.3 Hz, 2H), 7.59 (d, J = 8.7 Hz, 1H), 6.99 (d, J = 8.8 Hz, 1H), 3.98 (s, 3H), 2.91-2.83 (m, 2H), 1.63 (s × t, J = 7.5 Hz, 2H), 1.00 (t, J = 7.3 Hz, 3H). |
| 8 | 7-methoxy-N-(3-methylpyridin-4-yl)-2-oxo-8-propyl-2H-chromene-3-carboxamide | 3-methyl-pyridin-4-ylamine [CAS 1990-90-5] | (600 MHz, CDCl$_3$) δ 11.17 (s, 1H), 8.96 (s, 1H), 8.47-8.45 (m, 1H), 8.43 (d, J = 5.4 Hz, 2H), 8.43 (d, J = 5.4 Hz, 2H), 7.61 (d, J = 8.7 Hz, 1H), 7.00 (d, J = 8.7 Hz, 1H), 3.99 (s, 3H), 2.87 (dd, J = 6.9, 8.5 Hz, 2H), 2.42 (s, 3H), 1.63 (s × t, J = 7.5 Hz, 2H), 1.00 (t, J = 7.3 Hz, 3H). |
| 9 | 7-methoxy-2-oxo-8-propyl-N-[3-(trifluoromethyl)pyridin-4-yl]-2H-chromene-3-carboxamide | 3-trifluoromethyl-pyridin-4-ylamine [CAS 387824-61-5] | (600 MHz, CDCl$_3$) δ 11.68 (s, 1H), 8.93 (s, 1H), 8.85 (br s, 1H), 8.74 (d, J = 5.0 Hz, 1H), 8.68 (d, J = 5.6 Hz, 1H), 7.60 (d, J = 8.7 Hz, 1H), 7.00 (d, J = 8.8 Hz, 1H), 4.00 (s, 3H), 2.88-2.84 (m, 2H), 1.66-1.58 (m, 2H), 0.99 (t, J = 7.3 Hz, 3H). |
| 10 | 7-methoxy-2-oxo-8-propyl-N-pyridin-3-yl-2H-chromene-3-carboxamide | pyridin-3-ylamine [CAS 462-08-8] | (600 MHz, CDCl$_3$) δ 10.99 (s, 1H), 8.94 (s, 1H), 8.87 (br s, 1H), 8.41 (br. s., 1H), 8.28 (ddd, J = 1.3, 2.3, 8.3 Hz, 1H), 7.59 (d, J = 8.7 Hz, 1H), 7.34 (dd, J = 4.9, 8.1 Hz, 1H), 6.99 (d, J = 8.7 Hz, 1H), 3.99 (s, 3H), 2.91-2.85 (m, 2H), 1.68-1.59 (m, 2H), 1.00 (t, J = 7.3 Hz, 3H). |
| 11 | 7-methoxy-2-oxo-8-propyl-N-[2-(trifluoromethyl)pyridin-3-yl]-2H-chromene-3-carboxamide | 2-trifluoromethyl-pyridin-3-ylamine [CAS 106877-32-1] | (600 MHz, CDCl$_3$) δ 11.45 (s, 1H), 8.93 (s, 1H), 8.90 (d, J = 8.4 Hz, 1H), 8.48 (dd, J = 1.2, 4.6 Hz, 1H), 7.59 (d, J = 8.7 Hz, 1H), 7.55 (dd, J = 4.6, 8.4 Hz, 1H), 6.99 (d, J = 8.7 Hz, 1H), 3.99 (s, 3H), 2.89-2.85 (m, 2H), 1.67-1.59 (m, 2H), 1.00 (t, J = 7.3 Hz, 3H). |
| 12 | 7-methoxy-N-(3-methylpyridin-2-yl)-2-oxo-8-propyl-2H-chromene-3-carboxamide | 3-methyl-pyridin-2-ylamine [CAS 1603-40-3] | (600 MHz, CDCl$_3$) δ 10.94 (br s, 1H), 8.97 (s, 1H), 8.42 (d, J = 11.3 Hz, 1H), 7.59 (d, J = 8.7 Hz, 2H), 7.11 (br s, 1H), 6.98 (d, J = 8.8 Hz, 1H), 3.98 (s, 3H), 2.89-2.85 (m, 2H), 2.39 (s, 3H), 1.67-1.59 (m, 2H), 1.00 (t, J = 7.4 Hz, 3H). |
| 13 | N-(3-chloropyridazin-4-yl)-7-methoxy-2-oxo-8-propyl-2H- | 3-chloro-pyridazin-4-ylamine [CAS 55928-83-1] | (600 MHz, CDCl$_3$) δ 11.85 (s, 1H), 9.02 (d, J = 5.6 Hz, 1H), 8.92 (s, 1H), 8.71 (d, J = 5.6 Hz, 1H), 7.62 (d, J = 8.7 Hz, 1H), 7.01 (d, J = 8.7 Hz, 1H), ), |

TABLE 1-continued

| Compound number | IUPAC name | Reagent(s) used | $^1$H NMR δ (ppm) for Compound |
|---|---|---|---|
| | chromene-3-carboxamide | | 4.00 (s, 3H), 2.91-2.83 (m, 2H), 1.66-1.60 (m, 2H), 1.00 (t, J = 7.4 Hz, 3H). |
| 14 | N-(2-chloro-5-fluoropyridin-3-yl)-7-methoxy-2-oxo-8-propyl-2H-chromene-3-carboxamide | 2-chloro-5-fluoro-pyridin-3-ylamine [CAS 884495-37-8] | (600 MHz, CDCl$_3$) δ 11.63 (s, 1H), 8.92 (s, 1H), 8.85 (dd, J = 2.8, 10.1 Hz, 1H), 8.04 (d, J = 2.8 Hz, 1H), 7.60 (d, J = 8.7 Hz, 1H), 7.00 (d, J = 8.7 Hz, 1H), 3.99 (s, 3H), 2.89-2.84 (m, 2H), 1.63 (dq, J = 7.5, 15.1 Hz, 2H), 1.00 (t, J = 7.3 Hz, 3H). |
| 15 | 7-methoxy-N-(2-methylpyridin-3-yl)-2-oxo-8-propyl-2H-chromene-3-carboxamide | 2-methyl-pyridin-3-ylamine [CAS 3430-10-2] | (600 MHz, CDCl$_3$) δ 11.00 (s, 1H), 8.94 (s, 1H), 8.69-8.62 (m, 1H), 8.30 (dd, J = 1.5, 4.8 Hz, 1H), 7.59 (d, J = 8.7 Hz, 1H), 7.21 (dd, J = 4.8, 8.1 Hz, 1H), 6.99 (d, J = 8.7 Hz, 1H), 3.99 (s, 3H), 2.87 (dd, J = 6.9, 8.4 Hz, 2H), 2.70 (s, 3H), 1.72-1.56 (m, 2H), 1.00 (t, J = 7.3 Hz, 3H). |
| 16 | N-(2-bromopyridin-3-yl)-7-methoxy-2-oxo-8-propyl-2H-chromene-3-carboxamide | 2-bromopyridin-3-amine [CAS 39856-58-1] | (300 MHz, CDCl$_3$) δ 11.44 (s, 1H), 8.91 (s, 1H), 8.87 (dd, J = 1.5, 8.4 Hz, 1H), 8.13 (dd, J = 1.2, 4.2 Hz, 1H), 7.58 (d, J = 9.0 Hz, 1H), 7.30 (dd, J = 4.8, 8.1 Hz, 1H), 6.98 (d, J = 8.7 Hz, 1H), 3.98 (s, 3H), 2.85 (t, J = 7.8 Hz, 2H), 1.68-1.56 (m, 2H), 0.99 (t, J = 7.5 Hz, 3H). |
| 18 | N-(3-chloropyridin-4-yl)-7-methoxy-2-oxo-8-propyl-2H-chromene-3-carboxamide | 3-chloropyridin-4-amine [CAS 19798-77-7] | (300 MHz, DMSO-d$_6$) δ 11.54 (s, 1H), 9.03 (s, 1H), 8.64 (s, 1H), 8.51-8.46 (m, 2H), 7.96 (d, J = 8.7 Hz, 1H), 7.23 (d, J = 9.0 Hz, 1H), 3.95 (s, 3H), 2.72 (t, J = 7.8 Hz, 2H), 1.58-1.50 (m, 2H), 0.92 (t, J = 7.5 Hz, 3H). |
| 19 | N-(2-ethylphenyl)-7-methoxy-2-oxo-8-propyl-2H-chromene-3-carboxamide | 2-ethylaniline [CAS 578-54-1] | (300 MHz, CDCl$_3$) δ 10.88 (s, 1H), 8.95 (s, 1H), 8.29 (d, J = 8.1 Hz, 1H), 7.57 (d, J = 9.0 Hz, 1H), 7.29-7.24 (m, 2H), 7.12 (t, J = 7.5 Hz, 1H), 6.97 (d, J = 8.4 Hz, 1H), 3.97 (s, 3H), 2.89-2.76 (m, 4H), 1.69-1.56 (m, 2H), 1.32 (t, J = 7.8 Hz, 3H), 0.99 (t, J = 7.2 Hz, 3H). |
| 20 | N-(2-chlorophenyl)-7-methoxy-2-oxo-8-propyl-2H-chromene-3-carboxamide | 2-chloroaniline [CAS 95-51-2] | (300 MHz, CDCl$_3$) δ 11.42 (s, 1H), 8.93 (s, 1H), 8.60 (d, J = 7.8 Hz, 1H), 7.57 (d, J = 8.7 Hz, 1H), 7.43 (d, J = 7.5 Hz, 1H), 7.31 (t, J = 7.8 Hz, 1H), 7.08 (t, J = 8.1 Hz, 1H), 6.97 (d, J = 8.7 Hz, 1H), 3.97 (s, 3H), 2.86 (t, J = 7.5 Hz, 2H), 1.66-1.54 (m, 2H), 0.99 (t, J = 7.8 Hz, 3H). |
| 22 | N-(2-cyanophenyl)-7-methoxy-2-oxo-8-propyl-2H-chromene-3-carboxamide | 2-aminobenzonitrile [CAS 1885-29-6] | (300 MHz, DMSO-d$_6$) δ 11.31 (s, 1H), 9.00 (s, 1H), 8.41 (d, J = 8.1 Hz, 1H), 7.94 (d, J = 9.0 Hz, 1H), 7.85 (dd, J = 1.5, 8.1 Hz, 1H), 7.76-7.71 (m, 1H) 7.32 (t, J = 7.8 Hz, 1H), 7.22 (d, J = 9.0 Hz, 1H), 3.95 (s, 3H), 2.74 (t, J = 8.1 Hz, 2H), 1.59-1.49 (m, 2H), 0.92 (t, J = 7.5 Hz, 3H). |
| 23 | N-(2-chloro-5-methylpyridin-3-yl)-7-methoxy-2-oxo-8-propyl-2H-chromene-3-carboxamide | 2-chloro-5-methylaniline [CAS 95-81-8] | (300 MHz, CDCl$_3$) δ 11.45 (s, 1H), 8.90 (s, 1H), 8.77 (s, 1H), 7.98 (s, 1H), 7.58 (d, J = 8.7 Hz, 1H), 6.98 (d, J = 9.0 Hz, 1H), 3.98 (s, 3H), 2.86 (t, J = 7.8 Hz, 2H), 2.37 (s, 3H), 1.66-1.57 (m, 2H), 0.99 (t, J = 7.2 Hz, 3H). |
| 24 | 7-methoxy-2-oxo-8-propyl-N-(2-propylphenyl)-2H-chromene-3-carboxamide | 2-propylaniline [CAS 1821-39-2] | (600 MHz, CDCl$_3$) δ 10.85 (s, 1H), 8.95 (s, 1H), 8.28 (dd, J = 1.2, 8.4 Hz, 1H), 7.57 (d, J = 9.0 Hz, 1H), 7.27-7.24 (m, 1H), 7.22 (dd, J = 1.2, 7.8 Hz, 1H), 7.12-7.09 (m, 1H), 6.96 (d, J = 9.0 Hz, 1H), 3.97 (s, 3H), 2.88-2.85 (m, 2H), 2.74 (t, J = 7.2 Hz, 2H), |

TABLE 1-continued

| Compound number | IUPAC name | Reagent(s) used | $^1$H NMR δ (ppm) for Compound |
|---|---|---|---|
| | | | 1.74-1.68 (m, 2H), 1.66-1.60 (m, 2H), 1.04-0.98 (m, 6H). |
| 26 | 7-methoxy-N-(2-methylphenyl)-2-oxo-8-propyl-2H-chromene-3-carboxamide | o-toluidine [CAS 95-53-4] | (300 MHz, DMSO-d$_6$) δ 10.68 (s, 1H), 8.98 (s, 1H), 8.19 (d, J = 8.2 Hz, 1H), 7.93 (d, J = 8.5 Hz, 1H), 7.32-7.18 (m, 3H), 7.07 (d, J = 8.5 Hz, 1H), 3.95 (s, 3H), 2.75 (t, J = 6.9 Hz, 2H), 2.33 (s, 3H), 1.62-1.48 (m, 2H), 0.92 (t, J = 7.3 Hz, 3H). |
| 27 | 8-isopropoxy-7-methoxy-2-oxo-N-[2-(trifluoromethyl)pyridin-3-yl]-2H-chromene-3-carboxamide | Intermediate 4 (used in place of Intermediate 1) and 2-Trifluoromethyl-pyridin-3-ylamine [CAS 106877-32-1] | (300 MHz, CDCl$_3$) δ11.37 (s, 1H), 8.92 (s, 1H), 8.86 (d, J = 8.2 Hz, 1H), 8.47 (dd, J = 1.0, 4.5 Hz, 1H), 7.55 (dd, J = 4.5, 8.5 Hz, 1H), 7.45 (d, J = 8.6 Hz, 1H), 7.01 (d, J = 8.8 Hz, 1H), 4.71-4.54 (m, 1H), 4.00 (s, 3H), 1.39 (d, J = 6.2 Hz, 6H). |
| 28 | 8-isopropoxy-7-methoxy-N-(2-methylpyridin-3-yl)-2-oxo-2H-chromene-3-carboxamide | Intermediate 4 (used in place of Intermediate 1) and 2-Methyl-pyridin-3-ylamine [CAS 340-10-2] | (300 MHz, CDCl$_3$) δ 10.93 (s, 1H), 8.94 (s, 1 H), 8.63 (dd, J = 1.5, 8.2 Hz, 1H), 8.30 (dd, J = 1.5, 4.7 Hz, 1H), 7.46 (d, J = 8.8 Hz, 1H), 7.21 (dd, J = 4.8, 8.2 Hz, 1H), 7.02 (d, J = 8.8 Hz, 1H), 4.61 (dt, J = 6.2, 12.4 Hz, 1H), 4.00 (s, 3H), 2.69 (s, 3H), 1.41 (d, 6H). |
| 29 | 8-ethoxy-7-methoxy-N-(2-methylpyridin-3-yl)-2-oxo-2H-chromene-3-carboxamide | Intermediate 5 (used in place of Intermediate 1) and 2-Methyl-pyridin-3-ylamine [CAS 3430-10-2] | (600 MHz, CDCl$_3$) δ 10.93 (br s, 1H), 8.96-8.93 (m, 1H), 8.63 (d, J = 8.0 Hz, 1H), 8.31 (d, J = 3.5 Hz, 1H), 7.47 (d, J = 8.7 Hz, 1H), 7.21 (dd, J = 4.8, 8.0 Hz, 1H), 7.03 (d, J = 8.7 Hz, 1H), 4.30-4.22 (m, 2H), 4.02 (s, 3H), 2.69 (s, 3H), 1.48 (t, J = 7.0 Hz, 3H). |
| 30 | 8-ethoxy-7-methoxy-2-oxo-N-[2-(trifluoromethyl)pyridin-3-yl]-2H-chromene-3-carboxamide | Intermediate 5 (used in place of Intermediate 1) 2-Trifluoromethyl-pyridin-3-ylamine [106877-32-1] | (300 MHz, CDCl$_3$) δ 11.37 (s, 1H), 8.93 (s, 1H), 8.87 (d, J = 8.4 Hz, 1H), 8.58-8.41 (m, 1H), 7.56 (dd, J = 4.6, 8.4 Hz, 1H), 7.46 (d, J = 8.8 Hz, 1H), 7.02 (d, J = 8.8 Hz, 1H), 4.26 (q, J = 7.1 Hz, 2H), 4.02 (s, 3H), 1.47 (t, J = 7.0 Hz, 3H). |
| 31 | 8-ethoxy-7-methoxy-2-oxo-N-[2-(trifluoromethyl)phenyl]-2H-chromene-3-carboxamide | Intermediate 5 (used in place of Intermediate 1) and 2-Trifluoromethyl-phenylamine [CAS 95-53-4] | (600 MHz, CDCl$_3$) δ 11.17 (br s, 1H), 8.93 (s, 1H), 8.37 (d, J = 8.2 Hz, 1H), 7.68 (d, J = 7.6 Hz, 1H), 7.60 (t, J = 7.8 Hz, 1H), 7.45 (d, J = 8.8 Hz, 1H), 7.28 (t, J = 7.5 Hz, 1H), 7.01 (d, J = 8.8 Hz, 1H), 4.26 (q, J = 7.0 Hz, 2H), 4.01 (s, 3H), 1.47 (t, 3H). |
| 32 | 8-isopropoxy-7-methoxy-2-oxo-N-[2-(trifluoromethyl)phenyl]-2H-chromene-3-carboxamide | Intermediate 4 (used in place of Intermediate 1) and 2-trifluoromethoxy-phenylamine [CAS 88-17-5] | (600 MHz, CDCl$_3$) δ 11.18 (br s, 1H), 8.93 (s, 1H), 8.38 (d, J = 8.2 Hz, 1H), 7.68 (d, J = 7.8 Hz, 1H), 7.60 (t, J = 7.8 Hz, 1H), 7.44 (d, J = 8.8 Hz, 1H), 7.28 (t, J = 7.5 Hz, 1H), 7.01 (d, 1H) 4.63 (dt, J = 12.3, 6.2 Hz, 1H), 4.00 (s, 3 H), 1.42-1.36 (m, 7H). |
| 33 | 7-methoxy-N-(2-methoxyphenyl)-2-oxo-8-propyl-2H-chromene-3-carboxamide | 2-methoxy-phenylamine [CAS 90-04-0] | (600 MHz, CDCl$_3$) δ 11.35 (s, 1H), 8.91 (s, 1H), 8.58 (dd, J = 1.4, 8.0 Hz, 1H), 7.56 (d, J = 8.7 Hz, 1H), 7.13-7.07 (m, 1H), 7.04-6.98 (m, 1H), 6.98-6.92 (m, 2H), 3.97 (d, J = 10.3 Hz, 6H), 2.89-2.81 (m, 2H), 1.62 (s × t, J = 7.5 Hz, 2H), 0.99 (t, J = 7.3 Hz, 3H). |
| 34 | 7-methoxy-N-[2-(methylthio)phenyl]-2-oxo-8-propyl-2H-chromene-3-carboxamide | 2-methylsulfanyl-phenylamine [CAS 2987-53-3] | (600 MHz, CDCl$_3$) δ 11.48 (s, 1H), 8.94 (s, 1H), 8.52 (dd, J = 1.2, 8.2 Hz, 1H), 7.57 (d, J = 8.7 Hz, 1H), 7.53 (dd, J = 1.5, 7.8 Hz, 1H), 7.36-7.31 (m, 1H), 7.12 (td, J = 1.3, 7.6 Hz, 1H), 6.97 (d, J = 8.7 Hz, 1H), 3.97 (s, 3H), 2.86 (dd, J = 6.9, 8.5 Hz, 2H), 2.47 (s, 3H), 1.66-1.60 (m, 2H), 0.99 (t, J = 7.3 Hz, 3H). |

TABLE 1-continued

| Compound number | IUPAC name | Reagent(s) used | $^1$H NMR δ (ppm) for Compound |
|---|---|---|---|
| 35 | N-[2-(2-furyl)phenyl]-7-methoxy-2-oxo-8-propyl-2H-chromene-3-carboxamide | 2-furan-2-yl-phenylamine [CAS 55578-79-5] | (600 MHz, CDCl$_3$) δ 11.21 (s, 1H), 8.93 (s, 1H), 8.36 (d, J = 7.6 Hz, 1H), 7.65-7.62 (m, 2H), 7.55 (d, J = 8.7 Hz, 1H), 7.40-7.35 (m, 1H), 7.22 (td, J = 1.2, 7.6 Hz, 1H), 6.95 (d, J = 8.7 Hz, 1H), 6.73 (d, J = 3.4 Hz, 1H), 6.57 (dd, J = 1.8, 3.3 Hz, 1H), 3.97 (s, 3H), 2.86 (dd, J = 6.9, 8.5 Hz, 2H), 1.62 (s × t, J = 7.5 Hz, 2H), 0.99 (t, J = 7.3, 3H). |
| 36 | N-[4-(hydroxymethyl)phenyl]-7-methoxy-2-oxo-8-propyl-2H-chromene-3-carboxamide | (4-aminophenyl)methanol [CAS 623-04-1] | (300 MHz, DMSO-d$_6$) δ 10.90 (s, 1H), 8.93 (s, 1H), 7.74 (d, J = 8.5 Hz, 2H), 7.57 (d, J = 8.8 Hz, 1H), 7.38 (d, J = 8.5 Hz, 2H), 6.97 (d, J = 7.9 Hz, 1H), 4.69 (s, 2H), 3.97 (s, 3H), 2.86 (t, J = 7.8 Hz, 2H), 1.70-1.57 (m, 2H), 0.99 (t, J = 7.2 Hz, 3H). |
| 37 | 7-methoxy-N-{4-[(methylsulfonyl)amino]-2-(trifluoromethyl)phenyl}-2-oxo-8-propyl-2H-chromene-3-carboxamide | N-(4-amino-3-(trifluoromethyl)phenyl)methanesulfonamide [CAS 926228-44-6] | (300 MHz, CDCl$_3$ δ 11.28 (s, 1H), 8.94 (s, 1H), 8.37 (d, J = 8.7 Hz, 1H), 7.60-7.54 (m, 2H), 7.48-7.45 (m, 1H), 6.98 (d, J = 9.0 Hz, 1H), 6.68 (s, 1H), 3.98 (s, 3H), 3.05 (s, 3H), 2.85 (t, J = 7.5 Hz, 2H), 1.65-1.58 (m, 2H), 0.99 (t, J = 7.5 Hz, 3H). |
| 38 | N-[4-(aminosulfonyl)-2-bromophenyl]-7-methoxy-2-oxo-8-propyl-2H-chromene-3-carboxamide | 4-amino-3-bromobenzenesulfonamide [CAS 53297-69-1] | (300 MHz, DMSO-d$_6$) δ 11.41 (s, 1H), 9.03 (s, 1H), 8.70-8.66 (m, 1H), 8.10-8.08 (m, 1H), 7.96 (d, J = 8.4 Hz, 1H), 7.88-7.84 (m, 1H), 7.44 (s, 2H), 7.24 (d, J = 7.8 Hz, 1H), 3.96 (s, 3H), 2.80-2.65 (m, 2H), 1.60-1.50 (m, 2H), 0.92 (t, J = 6.9 Hz, 3H). |
| 39 | N-[4-(aminosulfonyl)-2-chlorophenyl]-7-methoxy-2-oxo-8-propyl-2H-chromene-3-carboxamide | 4-amino-3-chlorobenzenesulfonamide [CAS 53297-68-0] | (300 MHz, DMSO-d$_6$) δ 11.51 (s, 1H), 9.02 (s, 1H), 8.71 (d, J = 4.2 Hz, 1H), 7.96-7.94 (m, 2H), 7.81 (dd, J = 0.6, 4.2 Hz, 1H), 7.43 (s, 2H), 7.23 (d, J = 4.8 Hz, 1H), 3.95 (s, 3H), 2.73 (t, J = 3.9 Hz, 2H), 1.56-1.52 (m, 2H), 0.91 (t, J = 3.6 Hz, 3H). |
| 40 | N-[4-(aminosulfonyl)phenyl]-7-methoxy-2-oxo-8-propyl-2H-chromene-3-carboxamide | 4-aminobenzenesulfonamide [CAS 63-74-1] | (300 MHz, DMSO-d$_6$) δ 10.89 (s, 1H), 8.88 (s, 1H), 7.95-7.78 (m, 5H), 7.32 (s, 2H), 7.23 (d, J = 8.8 Hz, 1H), 3.96 (s, 3H), 2.80-2.70 (m, 2H), 1.61-1.51 (m, 2H), 0.93 (t, J = 7.4 Hz, 3H). |
| 43 | 7-methoxy-N-(2-methoxypyridin-3-yl)-2-oxo-8-propyl-2H-chromene-3-carboxamide | 2-methoxypyridin-3-amine [CAS 20265-38-7] | (600 MHz, CDCl$_3$) δ 11.28 (s, 1H), 8.87 (s, 1H), 8.76 (dd, J = 1.8, 7.8 Hz, 1H), 7.89 (dd, J = 1.8, 5.4 Hz, 1H), 7.54 (d, J = 9.0 Hz, 1H), 6.95-6.91 (m, 2H), 4.10 (s, 3H), 3.96 (s, 3H), 2.86-2.84 (m, 2H), 1.64-1.58 (m, 2H), 0.98 (t, J = 7.8 Hz, 3H). |
| 44 | 7-methoxy-N-{2-methoxy-4-[(methylsulfonyl)amino]phenyl}-2-oxo-8-propyl-2H-chromene-3-carboxamide | N-(5-amino-6-methoxypyridin-2-yl)methanesulfonamide [CAS 57165-06-7] | (300 MHz, DMSO-d$_6$) δ 11.10 (s, 1H), 9.64 (br s, 1H), 8.95 (s, 1H), 8.37 (d, J = 8.7 Hz, 1H), 7.91 (d, J = 8.7 Hz, 1H), 7.21 (d, J = 8.7 Hz, 1H) 6.93 (d, J = 2.4 Hz, 1H), 6.81 (dd, J = 2.4, 8.7 Hz, 1H), 3.94 (s, 3H), 3.87 (s, 3H), 2.96 (s, 3H), 2.73 (t, J = 6.9 Hz, 2H), 1.58-1.50 (m, 2H), 0.92 (t, J = 7.5 Hz, 3H). |
| 45 | N-(4-hydroxy-2-methylphenyl)-7-methoxy-2-oxo-8-propyl-2H-chromene-3-carboxamide | 4-amino-3-methylphenol [CAS 2835-99-6] | (300 MHz, DMSO-d$_6$) δ 10.38 (s, 1H), 9.25 (s, 1H), 8.92 (s, 1H), 7.90 (d, J = 8.7 Hz, 1H), 7.82 (d, J = 8.4 Hz, 1H), 7.20 (d, J = 8.4 Hz, 1H), 6.65-6.59 (m, 2H), 3.94 (s, 3H), 2.74 (t, J = 8.1 Hz, 2H), 2.22 (s, 3H), 1.58-1.50 (m, 2H), 0.92 (t, J = 7.8 Hz, 3H). |

TABLE 1-continued

| Compound number | IUPAC name | Reagent(s) used | $^1$H NMR δ (ppm) for Compound |
|---|---|---|---|
| 47 | N-[4-(acetylamino)-2-(trifluoromethyl)phenyl]-7-methoxy-2-oxo-8-propyl-2H-chromene-3-carboxamide | N-(4-amino-3-(trifluoromethyl)phenyl)acetamide [CAS 1579-89-1] | (300 MHz, CDCl$_3$) δ 11.18 (s, 1H), 8.91 (s, 1H), 8.31 (d, J = 9.3 Hz, 1H), 7.88 (s, 1H), 7.69 (d, J = 8.7 Hz, 1H), 7.56 (d, J = 8.7 Hz, 1H), 7.32 (s, 1H), 6.97 (d, J = 8.4 Hz, 1H), 3.97 (s, 3H), 2.88-2.81 (m, 2H), 2.20 (s, 3H), 1.65-1.58 (m, 2H), 0.98 (t, J = 7.5 Hz, 3H). |
| 48 | N-[2-(difluoromethoxy)phenyl]-7-methoxy-2-oxo-8-propyl-2H-chromene-3-carboxamide | 2-(difluoromethoxy)aniline [CAS 22236-04-0] | (300 MHz, CDCl$_3$) δ 11.37 (s, 1H), 8.90 (s, 1H), 8.61 (d, J = 8.1 Hz, 1H), 7.56 (d, J = 8.7 Hz, 1H), 7.29-7.21 (m, 2H), 7.14-7.09 (m, 1H), 6.96 (d, J = 8.7 Hz, 1H), 6.66 (t, J = 73.2 Hz, 1H), 3.96 (s, 3H), 2.85 (t, J = 7.5 Hz, 2H), 1.65-1.57 (m, 2H), 0.98 (t, J = 7.5 Hz, 3H). |
| 51 | N-[4-(acetylamino)-2-methylphenyl]-7-methoxy-2-oxo-8-propyl-2H-chromene-3-carboxamide | N-(4-amino-3-methylphenyl)acetamide [CAS 6375-20-8] | (300 MHz, CDCl$_3$) δ 10.81 (s, 1H), 8.93 (s, 1H), 8.23 (d, J = 8.7 Hz, 1H), 7.57 (d, J = 8.7 Hz, 1H), 7.51 (s, 1H), 7.26-7.24 (m, 1H), 7.13 (s, 1H), 6.97 (d, J = 8.7 Hz, 1H), 3.97 (s, 3H), 2.86 (t, J = 7.5 Hz, 2H), 2.41 (s, 3H), 2.17 (s, 3H), 1.66-1.56 (m, 2H), 0.99 (t, J = 7.2 Hz, 3H). |
| 54 | N-(2-formylpyridin-3-yl)-7-methoxy-2-oxo-8-propyl-2H-chromene-3-carboxamide | 3-aminopicolinaldehyde [CAS 55234-58-7] | (300 MHz, CDCl$_3$) δ 12.85 (s, 1H), 10.19 (s, 1H), 9.27 (d, J = 8.7 Hz, 1H), 8.87 (s, 1H), 8.54 (d, J = 4.5 Hz, 1H), 7.57-7.52 (m, 2H), 6.96 (d, J = 8.7 Hz, 1H), 3.97 (s, 3H), 2.86 (t, J = 7.5 Hz, 2H), 1.66-1.58 (m, 2H), 0.99 (t, J = 7.2 Hz, 3H). |
| 56 | N-{2-chloro-4-[(methylsulfonyl)amino]phenyl}-7-methoxy-2-oxo-8-propyl-2H-chromene-3-carboxamide | N-(4-amino-3-chlorophenyl)methanesulfonamide [CAS 57165-03-4] | (600 MHz, DMSO-d$_6$) δ 11.18 (s, 1H), 9.91 (s, 1H), 9.01 (s, 1H), 8.45 (d, J = 9.0 Hz, 1H), 7.95 (d, J = 9.0 Hz, 1H), 7.37 (s, 1H), 7.25-7.23 (m, 1H), 3.97 (s, 3H), 3.03 (s, 3H), 2.75 (t, J = 6.6 Hz, 2H), 1.58-1.54 (m, 2H), 0.93 (t, J = 7.8 Hz, 3H). |
| 57 | 7-methoxy-2-oxo-N-{4-[(piperidin-2-ylmethyl)amino]phenyl}-8-propyl-2H-chromene-3-carboxamide | tert-butyl 2-(((4-aminophenyl)amino)methyl)piperidine-1-carboxylate [CAS 1159976-36-9] followed by deprotection with HCl in CH$_2$Cl$_2$. | (600 MHz, CDCl$_3$) δ 10.64 (s, 1H), 8.90 (s, 1H), 7.57-7.49 (m, 3H), 6.96 (d, J = 8.8 Hz, 1H), 6.64 (d, J = 8.8 Hz, 2H), 4.03 (br. s., 1H), 3.97 (s, 3H), 3.17 (d, J = 12.6 Hz, 1H), 3.13-3.08 (m, 1H), 3.06-2.94 (m, 2H), 2.90-2.84 (m, 2H), 2.82-2.75 (m, 2H), 2.64 (td, J = 2.6, 11.8 Hz, 2H), 1.88-1.82 (m, 1H), 1.65-1.58 (m, 2H), 1.47-1.36 (m, 2H), 1.27-1.15 (m, 1H), 0.99 (t, J = 7.3 Hz, 3H). |
| 58 | 7-methoxy-2-oxo-N-{4-[(piperidin-3-ylmethyl)amino]phenyl}-8-propyl-2H-chromene-3-carboxamide | tert-butyl 3-(((4-aminophenyl)amino)methyl)piperidine-1-carboxylate [CAS 1159976-35-8] followed by deprotection with HCl in CH$_2$Cl$_2$ | (600 MHz, CDCl$_3$) δ 10.64 (s, 1H), 8.90 (s, 1H), 7.58-7.51 (m, 3H), 6.96 (d, J = 8.7 Hz, 1H), 6.61 (d, J = 8.8 Hz, 2H), 3.97 (s, 3H), 3.22-3.14 (m, 1H), 3.03 (d, J = 12.3 Hz, 2H), 3.01-2.96 (m, 2H), 2.89-2.84 (m, 2H), 2.63-2.57 (m, 1H), 2.40 (dd, J = 10.4, 11.7 Hz, 1H), 1.92 (dt, J = 1.8, 13.0 Hz, 1H), 1.80 (ddd, J = 3.6, 7.0, 13.9 Hz, 1H), 1.77-1.71 (m, 1H), 1.71-1.68 (m, 1H), 1.66-1.59 (m, 2H), 1.55-1.44 (m, 1H), 1.18 (qd, J = 3.8, 12.0 Hz, 1H), 0.99 (t, J = 7.3 Hz, 3H). |
| 59 | 7-methoxy-2-oxo-8-propyl-N-[4-(pyrrolidin-3-ylamino)phenyl]-2H-chromene-3-carboxamide | tert-butyl 3-((4-aminophenyl)amino)pyrrolidine-1-carboxylate [CAS 1159976-32-5] followed by deprotection with HCl in CH$_2$Cl$_2$. | (300 MHz, CDCl$_3$) δ 10.66 (s, 1H), 8.91 (s, 1H), 7.56 (d, J = 4.4 Hz, 1H), 7.54 (d, J = 4.7 Hz, 1H), 6.96 (d, J = 8.8 Hz, 1H), 6.63 (d, J = 8.8 Hz, 2H), 4.00-3.97 (m, 1H), 3.97 (s, 3H), 3.61 (q, J = 7.2 Hz, 1H), 3.18 (dd, J = 5.9, 11.4 Hz, 1H), 3.13 (ddd, J = 7.1, 7.5, |

TABLE 1-continued

| Compound number | IUPAC name | Reagent(s) used | $^1$H NMR δ (ppm) for Compound |
|---|---|---|---|
| | | | 10.6 Hz, 1H), 2.98 (ddd, J = 6.0, 8.3, 10.9 Hz, 1H), 2.90 (dd, J = 2.9, 11.4 Hz, 1H), 2.88-2.85 (m, 2H), 2.23-2.16 (m, 1H), 1.65-1.58 (m, 2H), 1.00 (t, J = 7.3 Hz, 3H). |
| 60 | 7-methoxy-2-oxo-N-[4-(piperidin-3-ylamino)phenyl]-8-propyl-2H-chromene-3-carboxamide | tert-butyl 3-((4-aminophenyl)amino)piperidine-1-carboxylate [CAS 1159976-34-7] followed by deprotection with HCl in CH$_2$Cl$_2$. | (600 MHz, CDCl$_3$) δ 10.64 (s, 1H), 8.90 (s, 1H), 7.54 (dd, J = 8.8, 14.4 Hz, 3H), 6.96 (d, J = 8.7 Hz, 1H), 6.64 (d, J = 9.0 Hz, 2H), 3.97 (s, 3H), 3.45 (d, J = 3.2 Hz, 1H), 3.23 (dd, J = 2.4, 11.6 Hz, 1H), 2.94-2.88 (m, 1H), 2.88-2.84 (m, 2H), 2.76-2.70 (m, 1H), 2.58 (dd, J = 7.6, 11.3 Hz, 1H), 1.98-1.92 (m, 1H), 1.80-1.70 (m, 5H), 1.62 (dq, J = 7.5, 15.0 Hz, 2H), 1.58-1.48 (m, 2H), 0.99 (t, J = 7.3 Hz, 3H). |
| 61 | (3S)-3-amino-4-[(4-{[(7-methoxy-2-oxo-8-propyl-2H-chromen-3-yl)carbonyl]amino}-3-methylphenyl)amino]-4-oxobutanoic acid | (S)-4-(tert-butoxy)-2-((tert-butoxycarbonyl)amino)-4-oxobutanoic acid [CAS 3057-74-7] followed by the deprotection with HCl in CH$_2$Cl$_2$. | (300 MHz, CDCl$_3$) δ 10.82 (s, 1H), 9.48 (s, 1H), 8.95 (s, 1H), 8.26 (d, J = 8.9 Hz, 1H), 7.64-7.60 (m, 1H), 7.58 (d, J = 8.8 Hz, 1H), 7.42-7.34 (m, 1H), 6.98 (d, J = 8.6 Hz, 1H), 3.98 (s, 3H), 3.84-3.73 (m, 1H), 3.69-3.62 (m, 1H), 2.93-2.80 (m, 2H), 2.73-2.60 (m, 1H), 2.43 (s, 3H), 1.69-1.59 (m, 2H), 1.00 (t, J = 7.3 Hz, 3H). |
| 62 | (4R)-4-amino-5-[(4-{[(7-methoxy-2-oxo-8-propyl-2H-chromen-3-yl)carbonyl]amino}-3-methylphenyl)amino]-5-oxopentanoic acid | (R)-5-(tert-butoxy)-2-((tert-butoxycarbonyl)amino)-5-oxopentanoic acid [CAS 104719-63-3] followed by the deprotection with HCl in CH$_2$Cl$_2$. | (600 MHz, DMSO-d$_6$, 1-drop of AcOD-d$_4$) δ 8.93 (s, 1H), 8.18 (d, J = 8.7 Hz, 1H), 7.85 (d, J = 8.7), 7.48 (s, 1H), 7.46 (d, J = 8.8 Hz, 1H), 7.16 (d, J = 8.7 Hz, 1H), 3.96 (t, J = 6.5 Hz, 1H), 3.93 (s, 3H), 2.74 (t, J = 7.5 Hz, 2H), 2.41-2.37 (m, 2H), 2.32 (s, 3H), 2.08 (q, J = 7.3 Hz, 2H), 1.58-1.49 (m, 2H), 0.91 (t, 3H). |
| 63 | N-[4-(aminosulfonyl)-2-methylphenyl]-7,8-diethoxy-2-oxo-2H-chromene-3-carboxamide | Intermediate 3 (used in place of Intermediate 1) and 4-amino-3-methylbenzenesulfonamide [CAS 53297-70-4] | (300 MHz, DMSO-d$_6$) δ 10.89 (s, 1H), 8.99 (s, 1H), 8.42 (d, J = 8.2 Hz, 1H), 7.79 (d, J = 9.1 Hz, 1H), 7.73-7.71 (m, 1H), 7.71-7.66 (m, 1H), 7.23-7.28 (m, 3H), 4.24 (q, J = 6.9 Hz, 2H), 4.12 (q, J = 7.0 Hz, 2H), 2.41 (s, 3H), 1.39 (t, J = 7.0 Hz, 3H), 1.32 (t, J = 7.0 Hz, 3H). |
| 64 | N-[4-(aminosulfonyl)-2-methylphenyl]-8-ethoxy-7-methoxy-2-oxo-2H-chromene-3-carboxamide | Intermediate 5 (used in place of Intermediate 1) and 4-amino-3-methylbenzenesulfonamide [CAS 53297-70-4 | (300 MHz, DMSO-d$_6$) δ 10.88 (s, 1H), 9.00 (s, 1H), 8.42 (d, J = 8.2 Hz, 1H), 7.81 (d, J = 9.1 Hz, 1H), 7.74-7.69 (m, 1H), 7.67 (d, J = 1.8 Hz, 1H), 7.28 (s, 1H), 7.26 (s, 2H), 4.11 (q, J = 7.0 Hz, 2H), 3.96 (s, 3H), 2.41 (s, 3H), 1.32 (t, J = 7.0 Hz, 3H). |
| 65 | N-[4-(aminosulfonyl)-2-methylphenyl]-8-isopropoxy-7-methoxy-2-oxo-2H-chromene-3-carboxamide | 8-isopropoxy-7-methoxy-2-oxo-2H-chromene-3-carboxylic acid and 4-amino-3-methylbenzenesulfonamide [CAS 53297-70-4] | (300 MHz, DMSO-d$_6$) δ 10.90 (s, 1H), 9.00 (s, 1H), 8.43 (d, J = 8.5 Hz, 1H), 7.81 (d, J = 9.1 Hz, 1H), 7.73-7.69 (m, 1H), 7.68-7.66 (m, 1H), 7.28 (s, 1H), 7.25 (s, 2H), 4.50-4.40 (m, 1H), 3.95 (s, 3H), 2.41 (s, 3H), 1.28 (d, J = 6.2 Hz, 6H). |
| 69 | 7,8-diethoxy-N-{4-[(methylsulfonyl)amino]-2-(trifluoromethyl)phenyl}-2-oxo-2H-chromene-3-carboxamide | Intermediate 3 (used in place of Intermediate 1) and N-(4-amino-3-(trifluoromethyl)phenyl)methanesulfonamide [CAS 926228-44-6] | (300 MHz, CDCl$_3$) δ 11.20 (s, 1H), 8.94 (s, 1H), 8.29 (d, J = 9.0 Hz, 1H), 7.56 (d, J = 2.4 Hz, 1H), 7.46-7.42 (m, 1H), 6.99 (d, J = 9.0 Hz, 1H), 6.94 (s, 1H), 4.28-4.20 (m, 4H), 3.05 (s, 3H), 1.55-1.43 (m, 6H). |
| 70 | 7-methoxy-2-oxo-8-propyl-N-[2-(trifluoromethoxy)phenyl]-2H- | 2-trifluoromethoxy-phenylamine [CAS 1535-75-7] | (600 MHz, CDCl$_3$) δ 11.41 (s, 1H), 8.92 (s, 1H), 8.65 (dd, J = 1.3, 8.2 Hz, 1H), 7.57 (d, J = 8.7 Hz, 1H), 7.38-7.30 (m, 2H), 7.18-7.11 (m, 1H), 6.97 (d, J = 8.7 Hz, |

| Compound number | IUPAC name | Reagent(s) used | $^1$H NMR δ (ppm) for Compound |
| --- | --- | --- | --- |
| | chromene-3-carboxamide | | 1H), 3.98 (s, 3H), 2.89-2.84 (m, 2H), 1.62 (s × t, J = 7.5 Hz, 2H), 1.00-0.97 (m, 2H). |
| 71 | N-[4-(aminosulfonyl)-2-methylphenyl]-8-ethyl-7-methoxy-2-oxo-2H-chromene-3-carboxamide | Intermediate 2 (used in place of Intermediate 1) and 4-amino-3-methylbenzenesulfonamide [CAS 53297-70-4] | (300 MHz, DMSO-d$_6$) δ 10.93 (s, 1H), 9.01 (s, 1H), 8.44 (d, J = 8.2 Hz, 1H), 7.95 (d, J = 8.8 Hz, 1H), 7.74-7.65 (m, 2H), 7.28-7.20 (m, 3H), 3.97 (s, 3H), 2.84-2.74 (m, 2H), 2.41 (s, 3H), 1.12 (t, J = 7.5 Hz, 3H). |
| 72 | N-[4-(aminosulfonyl)-2-(trifluoromethyl)phenyl]-7-methoxy-2-oxo-8-propyl-2H-chromene-3-carboxamide | 4-amino-3-trifluoromethylbenzenesulfonamide [CAS 39234-84-9] | (300 MHz, DMSO-d$_6$) δ 11.48 (s, 1H), 8.73 (s, 1H), 7.94 (d, J = 2.4 Hz, 1H), 7.84-7.79 (m, 2H), 7.18 (d, J = 9.3 Hz, 1H), 6.90 (d, J = 8.7 Hz, 1H), 6.73 (s, 1H), 3.92 (s, 1H), 2.69 (t, J = 7.8 Hz, 2H), 1.54-1.47 (m, 2H), 0.88 (t, J = 7.8 Hz, 3H). |

Example 6

Compound 17

N-(2-Ethylpyridin-3-yl)-7-methoxy-2-oxo-8-propyl-2H-chromene-3-carboxamide

Step 1: A mixture of 2-bromo-3-nitropyridine [CAS 19755-53-4] (0.600 g, 2.90 mmol), LiCl (0.80 g, 0.019 mmol), PdCl$_2$(PPh$_3$)$_2$ (0.20 g, 0.280 mmol) and tributyl(vinyl)stannane (1.0 g, 3.42 mmol) in DMF (5 mL) was heated at 90° C. overnight. After standard aqueous work up, the crude was purified by MPLC using (10% EtOAC/Hexanes) and gave a yellow oil.

Step 2: The yellow oil (0.25 g, 2.08 mmol) was hydrogenated at 50 psi over 10% Pd/C in MeOH (10 mL) for 16 hours. The mixture was then filtered and purified by MPLC using (5% MeOH in CH$_2$Cl$_2$) to give 2-ethylpyridin-3-amine as a solid.

Step 3: 2-Ethylpyridin-3-amine was substituted in the method used in Example 1.

$^1$H NMR (300 MHz, CDCl$_3$) δ 11.03 (s, 1H), 8.94 (s, 1H), 8.64 (d, J=8.1 Hz, 1H), 8.34 (d, J=4.8 Hz, 1H), 7.59 (d, J=8.7 Hz, 1H), 7.20 (dd, J=4.8, 8.4 Hz, 1H), 6.99 (d, J=8.7 Hz, 1H), 3.98 (s, 3H), 3.00 (q, J=7.5 Hz, 2H), 2.87 (t, J=7.8 Hz, 2H), 1.67-1.59 (m, 2H), 1.40 (t, J=7.5 Hz, 3H), 1.00 (t, J=7.5 Hz, 3H).

Example 7

Compound 21

(4-{[(7-Methoxy-2-oxo-8-propyl-2H-chromen-3-yl)carbonyl]amino}-3-methylphenyl)phosphonic acid Step 1: A solution of 4-iodo-2-methylaniline [CAS 13194-68-8] (0.51 g, 2.21 mmol), diethyl phosphonate (0.30 mL, 2.32 mmol), TEA (0.325 mL, 2.33 mmol), Pd(PPh$_3$)$_4$ (cat.) was heated at 90° C. overnight. The solution was cooled to room temperature and EtOAc was added. After standard aqueous work up, the crude was purified by MPLC (30-50% EtOAc/Hexanes) and used in the next step.

Step 2: Diethyl (4-amino-3-methylphenyl)phosphonate was substituted in the method used in Example 1.

Step 3: A solution of the previous amide from Step 2 (0.08, 0.164 mmol), bromotrimethylsilane (0.55 g, 3.41 mmol) in CH$_3$CN (5 mL) was heated at 80° C. overnight. After solution was allowed to cool to room temperature, evaporation to remove volatiles was done. The residue was purified by MPLC (NH$_3$/MeOH) followed by trituration in CHCl$_3$ then MeOH to give Compound 21 as a yellow solid.

$^1$H NMR (600 MHz, d-TFA) δ 9.32 (s, 1H), 8.24 (br s, 1H), 7.95-7.89 (m, 2H), 7.87 (d, J=9.0 Hz, 1H), 7.29 (d, J=8.4 Hz, 1H), 4.14 (s, 3H), 3.02 (t, J=6.6 Hz, 2H), 2.59 (s, 3H), 1.78-1.70 (m, 2H), 1.08 (t, J=7.2 Hz, 3H).

Example 8

Compound 25

(3-Chloro-4-{[(7-methoxy-2-oxo-8-propyl-2H-chromen-3-yl)carbonyl]amino}phenyl)boronic acid Step 1: 2-Chloro-4(4,4,5,5-tetramethyl-1,3,2-dioxaborolan-2-yl)aniline [CAS 721960-43-6] is substituted in the method used in Example 1.

Step 2: To a mixture of the amide from Step 1 (0.15 g, 0.302 mmol) in THF/MeOH/H$_2$O was added NaIO$_4$ (0.22 g, 1.03 mmol) at room temperature with stirring for 30 minutes. 1N HCl (0.30 mL, 0.30 mmol) was then added and stirring was allowed for 2 days. After 2 days water was added and the solid was filtered. The solid was washed with EtOAc and purified by MPLC (5% MeOH/CH$_2$Cl$_2$) to give the title compound.

$^1$H NMR (300 MHz, DMSO-d$_6$) δ 11.32 (s, 1H), 8.99 (s, 1H), 8.54-8.46 (m, 1H), 8.17 (s, 2H), 7.96-7.86 (m, 2H), 7.76-7.74 (m, 1H), 7.24-7.16 (m, 1H), 3.94 (s, 3H), 2.80-2.65 (m, 2H), 1.65-1.45 (m, 2H), 1.0-0.84 (m, 3H).

Example 9

Compound 41

N-(4-Amino-2-methylphenyl)-7-methoxy-2-oxo-8-propyl-2H-chromene-3-carboxamide Step 1: tert-Butyl (4-amino-3-methylphenyl)carbamate [CAS 325953-41-1] was substituted in the method used in Example 1.

Step 2: The compound from Step 1 (0.48 g, 1.03 mmol) in $CH_2Cl_2$ (25 mL) was treated with 4.0 M HCl in Dioxane (3.40 mL, 13.6 mmol) at room temperature and stirred overnight. The solution was evaporated and then triturated with ether followed by filtration to give the title compound.

$^1$H NMR (300 MHz, DMSO-$d_6$) δ 10.70 (s, 1H), 8.96 (s, 1H), 8.23 (d, J=9.6 Hz, 1H), 7.93 (d, J=8.7 Hz, 1H), 7.24-7.16 (m, 3H), 3.95 (s, 3H), 3.55 (br s, 3H), 2.73 (t, J=8.1 Hz, 2H), 2.34 (s, 3H), 1.56-1.53 (m, 2H), 0.92 (t, J=7.5 Hz, 3H).

Example 10

Compound 42

N-(6-Amino-2-methylpyridin-3-yl)-7-methoxy-2-oxo-8-propyl-2H-chromene-3-carboxamide Step 1: 6-Methyl-5-nitropyridin-2-amine [CAS 22280-62-2] (0.38 g, 2.48 mmol) was hydrogenated at 50 psi with 10% Pd/C (0.35 g) in MeOH/THF (10 mL) overnight to give 6-methylpyridine-2,5-diamine as a light yellow solid.

Step 2: 6-methylpyridine-2,5-diamine was substituted in the method used in Example 1. $^1$H NMR (300 MHz, $CDCl_3$) δ 10.61 (s, 1H), 8.90 (s, 1H), 8.15 (d, J=8.7 Hz, 1H), 7.56 (d, J=8.7 Hz, 1H), 6.97 (d, J=8.7 Hz, 1H), 6.43 (d, J=9.0 Hz, 1H), 4.39 (br s, 2H), 3.97 (s, 3H), 2.88-2.84 (m, 2H), 2.48 (s, 3H), 1.70-1.60 (m, 2H), 0.99 (t, J=7.2 Hz, 3H).

Example 11

Compound 46

7-Methoxy-N-{2-methyl-6-[(methylsulfonyl)amino]pyridin-3-yl}-2-oxo-8-propyl-2H-chromene-3-carboxamide Compound 42 (0.20 g, 0.545 mmol) was treated with TEA (0.15 mL, 1.08 mmol) and methanesulfonyl chloride (0.90 mL) in DMF (20 mL) at 0° C. The reaction was stirred overnight at room temperature then heated to 40° C. overnight. After standard aqueous workup, the crude was purified by MPLC (50% EtOAc/Hexanes) to give the title compound.

$^1$H NMR (600 MHz, DMSO-$d_6$) δ 10.55 (s, 1H), 10.39 (s, 1H), 8.93 (s, 1H), 8.27 (d, J=9.0 Hz, 1H), 7.90 (d, J=9.0 Hz, 1H), 7.20 (d, J=9.0 Hz, 1H), 6.87 (d, J=7.8 Hz, 1H), 3.94 (s, 3H), 3.29 (s, 3H), 2.73 (t, 7.8, 2H), 2.44 (s, 3H), 1.56-1.52 (m, 2H), 0.90 (t, J=7.8 Hz, 3H).

Compounds 49, 52 and 53 were prepared in a similar manner to the method described in Example 11 for Compound 46. The reagents used and the results are described below in Table 2.

TABLE 2

| Compound number | IUAPC name | Reagent (s) used | $^1$H NMR δ (ppm) for Compound |
|---|---|---|---|
| 49 | N-{4-[(ethylsulfonyl)amino]-2-methylphenyl}-7-methoxy-2-oxo-8-propyl-2H-chromene-3-carboxamide | Compound 41 was used in place of Compound 42 Ethanesulfonyl chloride was used in place of methanesulfonyl chloride | (300 MHz; $CDCl_3$) δ 10.86 (s, 1H), 8.95 (s, 1H), 8.23 (d, J = 8.4 Hz, 1H), 7.59 (d, J = 8.7 Hz, 1H), 7.15 (d, J = 2.4 Hz, 1H), 7.08 (dd, J = 2.4, 8.4 Hz, 1H), 6.98 (d, J = 9.0 Hz, 1H), 6.54 (s, 1H), 3.98 (s, 3H), 3.12 (q, J = 7.5 Hz, 2H), 2.88-2.84 (m, 2H), 2.41 (s, 3H), 1.70-1.57 (m, 2H), 1.38 (t, J = 7.2 Hz, 3H), 0.99 (t, J = 7.2 Hz, 3H). |
| 52 | 7-methoxy-N-{2-methyl-4-[(methylsulfonyl)amino]phenyl}-2-oxo-8-propyl-2H-chromene-3-carboxamide | Compound 41 was used in place of Compound 42 | (300 MHz, DMSO-$d_6$) δ 10.58 (s, 1H), 9.60 (br s, 1H), 8.94 (s, 1H), 8.08 (d, J = 8.1 Hz, 1H), 7.90 (d, J = 8.7 Hz, 1H), 7.20 (d, J = 8.7 Hz, 1H), 7.08-7.04 (m, 2H), 3.94 (s, 3H), 2.93 (s, 3H), 2.80-2.70 (m, 2H), 2.28 (s, 3H), 2.60-2.50 (m, 2H), 0.90 (t, J = 7.2 Hz, 3H). |
| 53 | 4-{[(7-methoxy-2-oxo-8-propyl-2H-chromen-3-yl)carbonyl]amino}-3-methylphenyl methanesulfonate | Compound 45 was used in place of Compound 42 | (300 MHz, $CDCl_3$) δ 10.94 (s, 1H), 8.94 (s, 1H), 8.40 (d, J = 9.3 Hz, 1H), 7.58 (d, J = 8.7 Hz, 1H), 7.18-7.15 (m, 2H), 6.98 (d, J = 9.0 Hz, 1H), 3.98 (s, 3H), 3.14 (s, 3H), 2.86 (t, J = 7.5 Hz, 2H), 2.45 (s, 3H), 1.66-1.59 (m, 2H), 0.99 (t, J = 7.2 Hz, 3H). |

Example 12

Compound 50

N-[4-Hydroxy-2-(trifluoromethyl)phenyl]-7-methoxy-2-oxo-8-propyl-2H-chromene-3-carboxamide Step 1: 4-amino-3-(trifluoromethyl)phenol [CAS 445-04-5] (0.292 g, 1.65 mmol), imidazole (0.280 g, 4.11 mmol), and tert-butylchlorodimethylsilane (0.36 g, 2.32 mmol) in DMF (5 mL) were stirred at room temperature overnight. After standard aqueous work up, the crude was purified by MPLC using (10% EtOAc/Hexanes) to give an orange oil.

Step 2: 4-((tert-butyldimethylsilyl)oxy)-2-(trifluoromethyl)aniline was substituted in the method used in Example 1.

Step 3: The compound from Step 2 (0.23 g, 0.430 mmol) in THF (5 mL) was treated with 1.0 M TBAF (0.480 mL, 0.480 mmol) solution in THF at 0° C. for 30 minutes. Solvent was removed and residue was purified by MPLC (40% EtOAc/Hexanes) to give the title compound.

$^1$H NMR (300 MHz, DMSO-$d_6$) δ 10.71 (s, 1H), 10.08 (s, 1H), 8.97 (s, 1H), 7.94-7.91 (m, 2H), 7.21 (d, J=8.7 Hz, 1H), 7.09-7.07 (m, 2H), 3.95 (s, 3H), 2.75-2.70 (m, 2H), 1.58-1.50 (m, 2H), 0.91 (t, J=7.2 Hz, 3H).

Example 13

Compound 55

7-Methoxy-N-{2-methyl-4-[(methylsulfonyl)methyl]phenyl}-2-oxo-8-propyl-2H-chromene-3-carboxamide Step 1: 4-(Bromomethyl)-2-methyl-1-nitrobenzene [CAS 141281-38-1] (1.45 g, 6.11 mmol) was added as a solid to sodium methanethiolate (0.50 g, 6.78 mmol) in DMF at 0° C. The reaction mixture was slowly warmed to room temperature overnight. After aqueous work up, crude was purified by MPLC (7.5% EtOAc/Hexanes) to give an oil which was used in the next step.

Step 2: To methyl(3-methyl-4-nitrobenzyl)sulfane (0.840 g, 4.26 mmol) in CH$_2$Cl$_2$ (15 mL) was added m-CPBA (3.0 eq) at room temperature for 2 hours. After aqueous work up, crude was purified by MPLC (60% EtOAc/Hexanes) which was used in the next step.

Step 3: The previous compound from step 2, was hydrogenated at 50 psi with 10% Pd/C (0.084 g) in MeOH/THF (30 mL) for 3.5 hours. The reaction mixture was filtered and purified by MPLC (1% MeOH/CH$_2$Cl$_2$) to give 2-methyl-4((methylsulfonyl)methyl) aniline as a light orange solid.

Step 4: 2-methyl-4-((methylsulfonyl)methyl)aniline was substituted in the method used in Example 1.

$^1$H NMR (300 MHz, DMSO-$d_6$) δ 10.74 (s, 1H), 8.98 (s, 1H), 8.24 (d, J=7.8 Hz, 1H), 7.93 (d, J=9.3 Hz, 1H), 7.29-7.21 (m, 3H), 4.41 (s, 2H), 3.95 (s, 3H), 2.89 (s, 3H), 2.80-2.71 (m, 2H), 2.34 (s, 3H), 1.60-1.50 (m, 2H), 0.92 (t, J=7.2 Hz, 3H).

Example 14

Compound 66

N-[4-(Aminosulfonyl)-2-methylphenyl]-7-methoxy-2-oxo-8-propyl-2H-chromene-3-carboxamide To a solution of Intermediate 1 (0.10 g, 0.381 mmol) in CH$_2$Cl$_2$ (5.0 mL) was added diisopropyl ethyl amine (0.1 mL, 0.572 mmol) and a 50% solution of propylphosphonic anhydride in ethyl acetate (0.340 mL, 0.572 mmol). The mixture was stirred for 30 minutes at room temperature. 4-Amino-3-methylbenzenesulfonamide [CAS #53297-70-4] (0.071 g, 0.381 mmol) was added to the reaction mixture at room temperature and stirred overnight. The reaction mixture was then poured onto ice water (25 mL) and CH$_2$Cl$_2$ (25 mL) added. The organic layer was separated and washed with brine (25 mL), dried with Na$_2$SO$_4$, filtered and concentrated to dryness. The residue was triturated with CH$_2$Cl$_2$/Hexanes and then the solid was purified with a MPLC to give the title compound as a white solid.

$^1$H NMR (300 MHz, DMSO-$d_6$) δ 10.95 (s, 1H), 9.03 (s, 1H), 8.46 (d, J=8.5 Hz, 1H), 7.97 (d, J=9.1 Hz, 1H), 7.79-7.65 (m, 2H), 7.33-7.18 (m, 3H), 3.98 (s, 3H), 2.81-2.71 (m, 2H), 2.43 (s, 3H), 1.64-1.50 (m, 2H), 0.94 (t, J=7.4 Hz, 3H).

Example 15

Compound 67

3-{[(4-{[(7-Methoxy-2-oxo-8-propyl-2H-chromen-3-yl)carbonyl]amino}-3-methylphenyl)sulfonyl]amino}propanoic acid Step 1: To a solution of 7-methoxy-N-(2-methylphenyl)-2-oxo-8-propyl-2H-chromene-3-carboxamide prepared following the procedure in WO2009019167 (0.104 g, 0.296 mmol) in CH$_2$Cl$_2$ (5.0 mL) was added chlorosulfonic acid (0.196 mL, 2.96 mmol) in CH$_2$Cl$_2$ (1.5 mL) dropwise at 0° C. The mixture was allowed to warm to room temperature and stirred overnight. The reaction mixture was cooled to 0° C. and carefully quenched with ice water (25 mL) and diluted with CH$_2$Cl$_2$ (25 mL). The organic layer is separated and washed with brine (25 mL), dried with Na$_2$SO$_4$, filtered and concentrated to dryness. The yellow solid, 4-(7-methoxy-2-oxo-8-propyl-2H-chromene-3-carboxamido)-3-methylbenzene-1-sulfonyl chloride was used as such in the next steps.

Step 2: To a solution of 4-(7-methoxy-2-oxo-8-propyl-2H-chromene-3-carboxamido)-3-methylbenzene-1-sulfonyl chloride (0.054 g, 0.122 mmol) in THF (7.0 mL) was added tert-butyl-3-aminopropanoate hydrochloride (0.028 g, 0.152 mmol) and diisopropylethylamine (0.086 mL, 0.500 mmol). After stirring at room temperature over night the solvent was concentrated to dryness and re-dissolved in CH$_2$Cl$_2$ and washed with water. The organic layer was separated and dried with Na$_2$SO$_4$, filtered and concentrated to dryness to give a white solid.

$^1$H NMR (300 MHz, DMSO-$d_6$) δ 10.97 (s, 1H), 9.02 (s, 1H), 8.50 (d, J=8.8 Hz, 1H), 7.96 (d, J=8.8 Hz, 1H), 7.69 (br s, 2H), 7.65 (s, 1H), 7.24 (d, J=8.8 Hz, 1H), 3.96 (s, 3H), 2.87-2.96 (m, 2H), 2.79-2.70 (m, 2H), 2.42 (s, 3H), 2.33 (t, J=7.3 Hz, 2H), 1.60-1.48 (m, 2H), 1.37 (s, 9H), 0.92 (t, J=7.3 Hz, 3H).

Step 3: The solid was dissolved in CH$_2$Cl$_2$ (4.5 mL) and treated with TFA (0.5 mL). After stirring at room temperature for 5 hours the solvent was concentrated to dryness to give the title compound as a yellow solid.

$^1$H NMR (300 MHz, DMSO-$d_6$) δ 10.91 (s, 1H), 8.96 (s, 1H), 8.44 (d, J=8.2 Hz, 1H), 7.91 (d, J=10.0 Hz, 1H), 7.64 (br s, 1H), 7.60 (s, 1H), 7.50 (t, J=6.0 Hz, 1H), 7.18 (d, J=10.0 Hz, 1H), 3.91 (s, 3H), 2.92-2.82 (m, 2H), 2.64-2.73 (m, 2H), 2.37 (s, 4H), 2.34-2.20 (m, 3H), 1.57-1.43 (m, 2H), 0.87 (t, J=7.5 Hz, 3H).

Example 16

Compound 68

7-Methoxy-N-{2-methyl-4-[(methylamino)sulfonyl]phenyl}-2-oxo-8-propyl-2H-chromene-3-carboxamide Compound 68 was prepared by substituting methylamine in Step 2 in the method of Example 15 for Compound 67.
$^1$H NMR (300 MHz, DMSO-$d_6$) δ 10.97 (s, 1H), 9.01 (s, 1H), 8.50 (d, J=8.8 Hz, 1H), 7.96 (d, J=8.5 Hz, 1H), 7.67 (s, 1H), 7.64 (s, 1H), 7.32 (d, J=4.7 Hz, 1H), 7.24 (d, J=9.1 Hz, 1H), 3.96 (s, 3H), 2.74 (t, J=7.0 Hz, 2H), 2.42 (s, 3H), 1.62-1.49 (m, 2H), 0.92 (t, J=7.3 Hz, 3H).

Example 17

GTP γ$^{35}$S Binding Assay

The S1P1 activity of the compounds according to the invention, were tested using the GTP γ$^{35}$S binding assay. The compounds were assessed for their ability to activate or block activation of the human S1P1 receptor in cells stably expressing the S1P1 receptor. Some of the results are presented in Table 3.

GTP γ$^{35}$S binding was measured in the medium containing (mM) HEPES 25, pH 7.4, MgCl$_2$ 10, NaCl 100, dithiothreitol 0.5, digitonin 0.003%, 0.2 nM GTP γ$^{35}$S, and 5 μg membrane protein in a volume of 150 μl. Test compounds were included in the concentration range from 0.08 to 5,000 nM unless indicated otherwise. Membranes were incubated with 100 μM 5'-adenylylimidodiphosphate for 30 min, and subsequently with 10 μM GDP for 10 min on ice. Drug solutions and membrane were mixed, and then reactions were initiated by adding GTP γ$^{35}$S and continued for 30 min at 25° C. Reaction mixtures were filtered over Whatman GF/B filters under vacuum, and washed three times with 3 mL of ice-cold buffer (HEPES 25, pH7.4, MgCl$_2$ 10 and NaCl 100). Filters were dried and mixed with scintillant, and counted for $^{35}$S activity using a β-counter. Agonist-induced GTP γ$^{35}$S binding was obtained by subtracting that in the absence of agonist. Binding data were analyzed using a non-linear regression method. In case of antagonist assay, the reaction mixture contained 10 nM S1P in the presence of test antagonist at concentrations ranging from 0.08 to 5000 nM.

Activity Potency:
S1P1 receptor from GTP γ$^{35}$S: nM, (EC$_{50}$),

TABLE 3

| Compound number | IUPAC name | EC$_{50}$ (nM) |
|---|---|---|
| 6 | N-(3-bromopyridin-4-yl)-7-methoxy-2-oxo-8-propyl-2H-chromene-3-carboxamide | 19.0 |
| 5 | N-(2-bromophenyl)-7-methoxy-2-oxo-8-propyl-2H-chromene-3-carboxamide | 26.4 |
| 62 | (4R)-4-amino-5-[(4-{[(7-methoxy-2-oxo-8-propyl-2H-chromen-3-yl)carbonyl]amino}-3-methylphenyl)amino]-5-oxopentanoic acid | 3.1 |
| 38 | N-[4-(aminosulfonyl)-2-bromophenyl]-7-methoxy-2-oxo-8-propyl-2H-chromene-3-carboxamide | 3.5 |
| 49 | N-[4-(aminosulfonyl)-2-methylphenyl]-7-methoxy-2-oxo-8-propyl-2H-chromene-3-carboxamide | 14.3 |

Example 18

Lymphopenia Assay in Mice

Test drugs are prepared in a solution containing 3% (w/v) 2-hydroxy propyl β-cyclodextrin (HPBCD) and 1% DMSO to a final concentration of 1 mg/ml, and subcutaneously injected to female C57BL6 mice (CHARLES RIVERS) weighing 20-25 g at the dose of 10 mg/Kg. Blood samples are obtained by puncturing the submandibular skin with a Goldenrod animal lancet at 5, 24, 48, 72, and 96 hrs post drug application. Blood is collected into microvettes (SARSTEDT) containing EDTA tripotassium salt. Lymphocytes in blood samples are counted using a HEMAVET Multispecies Hematology System, HEMAVET HV950FS (Drew Scientific Inc.). (Hale, J. et al Bioorg. & Med. Chem. Lett. 14 (2004) 3351).

What is claimed is:

1. A method of treating a disorder associated with sphingosine-1-phosphate 1 (S1P1) receptor modulation, the method comprising administering to a mammal in need thereof a pharmaceutical composition comprising a therapeutically effective amount of a compound of Formula I:

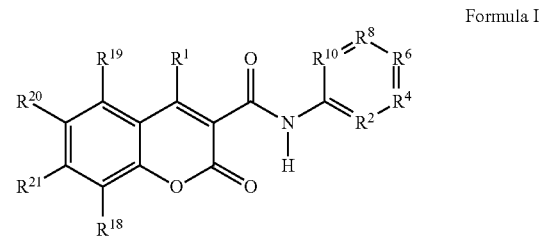

Formula I wherein:
$R^1$ is hydrogen, halogen or $C_{1-6}$ alkyl;
$R^2$ is $CR^3$ or N;
$R^3$ is hydrogen, halogen, O($C_{1-6}$ alkyl), S($C_{1-6}$ alkyl), cyano, aldehyde, heterocycle, $C_{1-6}$ alkyl or hydroxyl;
$R^4$ is $CR^5$ or N;
$R^5$ is hydrogen, halogen, hydroxyl or non-substituted $C_{1-6}$ alkyl;
$R^6$ is $CR^7$ or N;
$R^7$ is —NHR$^{12}$, —S(O)$_2$R$^{14}$, —C(O)NHR$^{16}$, —OR$^{17}$, hydrogen, halogen, phosphonic acid, boronic acid, —CH$_2$—OH, —CH$_2$—S(O)$_2$CH$_3$, —(CH$_2$)$_a$—NH—(CH$_2$)$_b$—O$_c$—P(O)(OH)$_2$, —(CH$_2$)$_d$—C(NH$_2$)(CH$_2$OH)(CH$_2$—O—P(O)(OH)$_2$), —(CH$_2$)$_e$—C(NH$_2$)(CH$_3$)(CH$_2$—O—P(O)(OH)$_2$) or —(CH$_2$)$_f$NH—(CH$_2$)$_g$—SO$_3$H;
a is 1 or 2;
b is 2 or 3;
c is 0 or 1;
d is 0 or 1;
e is 0 or 1;
f is 0 or 1;
g is 2 or 3;
$R^8$ is $CR^9$ or N;
$R^9$ is hydrogen, halogen, non-substituted $C_{1-6}$ alkyl or hydroxyl;
$R^{10}$ is $CR^{11}$ or N;
$R^{11}$ is hydrogen, halogen or $C_{1-6}$ alkyl;
$R^{12}$ is hydrogen, $C_{1-6}$ alkyl, —C(O)R$^{13}$, —S(O)$_2$(C$_{1-3}$ alkyl) or heterocycle;
$R^{13}$ is amino or $C_{1-6}$ alkyl;

$R^{14}$ is $C_{1-4}$ alkyl, $NHR^{15}$ or hydroxyl;
$R^{15}$ is hydrogen or $C_{1-6}$ alkyl;
$R^{16}$ is hydrogen or $C_{1-6}$ alkyl;
$R^{17}$ is hydrogen, $C_{1-6}$ alkyl or —S(O)$_2$(C$_{1-3}$ alkyl);
$R^{18}$ is $C_{2-4}$ alkyl or —OC$_{2-4}$ alkyl;
$R^{19}$ is hydrogen, halogen or $C_{1-6}$ alkyl;
$R^{20}$ is hydrogen, halogen or $C_{1-6}$ alkyl; and
$R^{21}$ is —C$_{1-4}$ alkyl;
wherein each said alkyl is optionally substituted with halogen, hydroxyl, cycloalkyl, amino, non-aromatic heterocycle, carboxylic acid, phosphonic acid, sulphonic acid or phosphoric acid, unless otherwise specified;

or an enantiomer, diastereoisomer, hydrate, solvate, crystal form, isomer or tautomer thereof;
or a pharmaceutically acceptable salt of any of the foregoing, wherein the disorder is selected from the group consisting of inflammatory bowel disease and ulcerative colitis.

2. The method of claim 1, wherein:
$R^1$ is hydrogen;
$R^2$ is $CR^3$;
$R^3$ is halogen, O(C$_{1-6}$ alkyl), S(C$_{1-6}$ alkyl), cyano, aldehyde, heterocycle or $C_{1-6}$ alkyl;
$R^4$ is $CR^5$ or N;
$R^5$ is hydrogen or halogen;
$R^6$ is $CR^7$ or N;
$R^7$ is —NHR$^{12}$, —S(O)$_2$R$^{14}$, —OR$^{17}$, hydrogen, phosphonic acid, boronic acid, —CH$_2$—OH or —CH$_2$—S(O)$_2$CH$_3$;
$R^8$ is $CR^9$ or N;
$R^9$ is hydrogen, halogen or non-substituted $C_{1-6}$ alkyl;
$R^{10}$ is $CR^{11}$;
$R^{11}$ is hydrogen, halogen or $C_{1-6}$ alkyl;
$R^{12}$ is —S(O)$_2$(C$_{1-3}$ alkyl), C(O)R$^{13}$ or heterocycle;
$R^{13}$ is $C_{1-6}$ alkyl;
$R^{14}$ is $NHR^{15}$;
$R^{15}$ is hydrogen or $C_{1-6}$ alkyl;
$R^{16}$ is $C_{1-6}$ alkyl;
$R^{17}$ is hydrogen or —S(O)$_2$(C$_{1-3}$ alkyl);
$R^{18}$ is $C_{2-4}$ alkyl or —OC$_{2-4}$ alkyl;
$R^{19}$ is hydrogen;
$R^{20}$ is hydrogen; and
$R^{21}$ is —OC$_{1-4}$ alkyl.

3. The method of claim 1, wherein:
$R^1$ is hydrogen;
$R^2$ is $CR^3$;
$R^3$ is halogen, —O(C$_{1-6}$ alkyl) or $C_{1-6}$ alkyl;
$R^4$ is $CR^5$ or N;
$R^5$ is hydrogen;
$R^6$ is $CR^7$ or N;
$R^7$ is —NHR$^{12}$, —S(O)$_2$R$^{14}$, —OR$^{17}$, hydrogen, phosphonic acid or boronic acid;
$R^8$ is $CR^9$;
$R^9$ is hydrogen;
$R^{10}$ is $CR^{11}$;
$R^{11}$ is hydrogen or $C_{1-6}$ alkyl;
$R^{12}$ is —S(O)$_2$(C$_{1-3}$ alkyl) or C(O)R$^{13}$;
$R^{13}$ is $C_{1-6}$ alkyl;
$R^{14}$ is $NHR^{15}$;
$R^{15}$ is hydrogen;
$R^{17}$ is hydrogen;
$R^{18}$ is $C_{2-4}$ alkyl or —OC$_{2-4}$ alkyl;
$R^{19}$ is hydrogen;
$R^{20}$ is hydrogen; and
$R^{21}$ is —OC$_{1-4}$ alkyl.

4. The method of claim 1, wherein the compound is selected from:

(3-chloro-4-{[(7-methoxy-2-oxo-8-propyl-2H-chromen-3-yl)carbonyl]amino}phenyl)boronic acid;
(3S)-3-amino-4-[(4-{[(7-methoxy-2-oxo-8-propyl-2H-chromen-3-yl)carbonyl]amino}-3-methylphenyl)amino]-4-oxobutanoic acid;
(4-{[(7-methoxy-2-oxo-8-propyl-2H-chromen-3-yl)carbonyl]amino}-3-methylphenyl)phosphonic acid;
(4R)-4-amino-5-[(4-{[(7-methoxy-2-oxo-8-propyl-2H-chromen-3-yl)carbonyl]amino}-3-methylphenyl)amino]-5-oxopentanoic acid;
3-{[(4-{[(7-methoxy-2-oxo-8-propyl-2H-chromen-3-yl)carbonyl]amino}-3-methylphenyl)sulfonyl]amino}propanoic acid;
4-{[(7-methoxy-2-oxo-8-propyl-2H-chromen-3-yl)carbonyl]amino}-3-methylphenyl methanesulfonate;
7,8-diethoxy-N-{4-[(methylsulfonyl)amino]-2-(trifluoromethyl)phenyl}-2-oxo-2H-chromene-3-carboxamide;
7-methoxy-2-oxo-8-propyl-N-(2-propylphenyl)-2H-chromene-3-carboxamide;
7-methoxy-2-oxo-8-propyl-N-[2-(trifluoromethoxy)phenyl]-2H-chromene-3-carboxamide;
7-methoxy-2-oxo-8-propyl-N-[2-(trifluoromethyl)phenyl]-2H-chromene-3-carboxamide;
7-methoxy-2-oxo-8-propyl-N-[2-(trifluoromethyl)pyridin-3-yl]-2H-chromene-3-carboxamide;
7-methoxy-2-oxo-8-propyl-N-[3-(trifluoromethyl)pyridin-4-yl]-2H-chromene-3-carboxamide;
7-methoxy-2-oxo-8-propyl-N-[4-(pyrrolidin-3-ylamino)phenyl]-2H-chromene-3-carboxamide;
7-methoxy-2-oxo-8-propyl-N-pyridin-3-yl-2H-chromene-3-carboxamide;
7-methoxy-2-oxo-8-propyl-N-pyridin-4-yl-2H-chromene-3-carboxamide;
7-methoxy-2-oxo-N-[4-(piperidin-3-ylamino)phenyl]-8-propyl-2H-chromene-3-carboxamide;
7-methoxy-2-oxo-N-{4-[(piperidin-2-ylmethyl)amino]phenyl}-8-propyl-2H-chromene-3-carboxamide;
7-methoxy-2-oxo-N-{4-[(piperidin-3-ylmethyl)amino]phenyl}-8-propyl-2H-chromene-3-carboxamide;
7-methoxy-N-(2-methoxyphenyl)-2-oxo-8-propyl-2H-chromene-3-carboxamide;
7-methoxy-N-(2-methoxypyridin-3-yl)-2-oxo-8-propyl-2H-chromene-3-carboxamide;
7-methoxy-N-(2-methylphenyl)-2-oxo-8-propyl-2H-chromene-3-carboxamide;
7-methoxy-N-(2-methylpyridin-3-yl)-2-oxo-8-propyl-2H-chromene-3-carboxamide;
7-methoxy-N-(3-methylpyridin-2-yl)-2-oxo-8-propyl-2H-chromene-3-carboxamide;
7-methoxy-N-(3-methylpyridin-4-yl)-2-oxo-8-propyl-2H-chromene-3-carboxamide;
7-methoxy-N-[2-(methylthio)phenyl]-2-oxo-8-propyl-2H-chromene-3-carboxamide;
7-methoxy-N-{2-methoxy-4-[(methylsulfonyl)amino]phenyl}-2-oxo-8-propyl-2H-chromene-3-carboxamide;
7-methoxy-N-{2-methyl-4-[(methylamino)sulfonyl]phenyl}-2-oxo-8-propyl-2H-chromene-3-carboxamide;
7-methoxy-N-{2-methyl-4-[(methylsulfonyl)amino]phenyl}-2-oxo-8-propyl-2H-chromene-3-carboxamide;
7-methoxy-N-{2-methyl-4-[(methylsulfonyl)methyl]phenyl}-2-oxo-8-propyl-2H-chromene-3-carboxamide;
7-methoxy-N-{2-methyl-6-[(methylsulfonyl)amino]pyridin-3-yl}-2-oxo-8-propyl-2H-chromene-3-carboxamide;

7-methoxy-N-{4-[(methylsulfonyl)amino]-2-(trifluoromethyl)phenyl}-2-oxo-8-propyl-2H-chromene-3-carboxamide;
8-ethoxy-7-methoxy-2-oxo-N-[2-(trifluoromethyl)phenyl]-2H-chromene-3-carboxamide;
8-ethoxy-7-methoxy-2-oxo-N-[2-(trifluoromethyl)pyridin-3-yl]-2H-chromene-3-carboxamide;
8-ethoxy-7-methoxy-N-(2-methylpyridin-3-yl)-2-oxo-2H-chromene-3-carboxamide;
8-isopropoxy-7-methoxy-2-oxo-N-[2-(trifluoromethyl)phenyl]-2H-chromene-3-carboxamide;
8-isopropoxy-7-methoxy-2-oxo-N-[2-(trifluoromethyl)pyridin-3-yl]-2H-chromene-3-carboxamide;
8-isopropoxy-7-methoxy-N-(2-methylpyridin-3-yl)-2-oxo-2H-chromene-3-carboxamide;
N-(2-bromophenyl)-7-methoxy-2-oxo-8-propyl-2H-chromene-3-carboxamide;
N-(2-bromopyridin-3-yl)-7-methoxy-2-oxo-8-propyl-2H-chromene-3-carboxamide;
N-(2-chloro-5-fluoropyridin-3-yl)-7-methoxy-2-oxo-8-propyl-2H-chromene-3-carboxamide;
N-(2-chloro-5-methylpyridin-3-yl)-7-methoxy-2-oxo-8-propyl-2H-chromene-3-carboxamide;
N-(2-chlorophenyl)-7-methoxy-2-oxo-8-propyl-2H-chromene-3-carboxamide;
N-(2-chloropyridin-3-yl)-7-methoxy-2-oxo-8-propyl-2H-chromene-3-carboxamide;
N-(2-cyanophenyl)-7-methoxy-2-oxo-8-propyl-2H-chromene-3-carboxamide;
N-(2-ethylphenyl)-7-methoxy-2-oxo-8-propyl-2H-chromene-3-carboxamide;
N-(2-ethylpyridin-3-yl)-7-methoxy-2-oxo-8-propyl-2H-chromene-3-carboxamide;
N-(2-fluorophenyl)-7-methoxy-2-oxo-8-propyl-2H-chromene-3-carboxamide;
N-(2-formylpyridin-3-yl)-7-methoxy-2-oxo-8-propyl-2H-chromene-3-carboxamide;
N-(3-bromopyridin-4-yl)-7-methoxy-2-oxo-8-propyl-2H-chromene-3-carboxamide;
N-(3-chloropyridazin-4-yl)-7-methoxy-2-oxo-8-propyl-2H-chromene-3-carboxamide;
N-(3-chloropyridin-4-yl)-7-methoxy-2-oxo-8-propyl-2H-chromene-3-carboxamide;
N-(3-fluoro-2-methylphenyl)-7-methoxy-2-oxo-8-propyl-2H-chromene-3-carboxamide;
N-(4-amino-2-methylphenyl)-7-methoxy-2-oxo-8-propyl-2H-chromene-3-carboxamide;
N-(4-hydroxy-2-methyl phenyl)-7-methoxy-2-oxo-8-propyl-2H-chromene-3-carboxamide;
N-(6-amino-2-methylpyridin-3-yl)-7-methoxy-2-oxo-8-propyl-2H-chromene-3-carboxamide;
N-[2-(2-furyl)phenyl]-7-methoxy-2-oxo-8-propyl-2H-chromene-3-carboxamide;
N-[2-(difluoromethoxy)phenyl]-7-methoxy-2-oxo-8-propyl-2H-chromene-3-carboxamide;
N-[4-(acetylamino)-2-(trifluoromethyl)phenyl]-7-methoxy-2-oxo-8-propyl-2H-chromene-3-carboxamide;
N-[4-(acetylamino)-2-methylphenyl]-7-methoxy-2-oxo-8-propyl-2H-chromene-3-carboxamide;
N-[4-(aminosulfonyl)-2-(trifluoromethyl)phenyl]-7-methoxy-2-oxo-8-propyl-2H-chromene-3-carboxamide;
N-[4-(aminosulfonyl)-2-bromophenyl]-7-methoxy-2-oxo-8-propyl-2H-chromene-3-carboxamide;
N-[4-(aminosulfonyl)-2-chlorophenyl]-7-methoxy-2-oxo-8-propyl-2H-chromene-3-carboxamide;
N-[4-(aminosulfonyl)-2-methylphenyl]-7,8-diethoxy-2-oxo-2H-chromene-3-carboxamide;
N-[4-(aminosulfonyl)-2-methylphenyl]-7-methoxy-2-oxo-8-propyl-2H-chromene-3-carboxamide;
N-[4-(aminosulfonyl)-2-methylphenyl]-8-ethoxy-7-methoxy-2-oxo-2H-chromene-3-carboxamide;
N-[4-(aminosulfonyl)-2-methylphenyl]-8-ethyl-7-methoxy-2-oxo-2H-chromene-3-carboxamide;
N-[4-(aminosulfonyl)-2-methylphenyl]-8-isopropoxy-7-methoxy-2-oxo-2H-chromene-3-carboxamide;
N-[4-(aminosulfonyl)phenyl]-7-methoxy-2-oxo-8-propyl-2H-chromene-3-carboxamide;
N-[4-(hydroxymethyl)phenyl]-7-methoxy-2-oxo-8-propyl-2H-chromene-3-carboxamide;
N-[4-hydroxy-2-(trifluoromethyl)phenyl]-7-methoxy-2-oxo-8-propyl-2H-chromene-3-carboxamide;
N-{2-chloro-4-[(methylsulfonyl)amino]phenyl}-7-methoxy-2-oxo-8-propyl-2H-chromene-3-carboxamide; and
N-{4-[(ethylsulfonyl)amino]-2-methylphenyl}-7-methoxy-2-oxo-8-propyl-2H-chromene-3-carboxamide;
and pharmaceutically acceptable salts thereof.

5. The method of claim 1, wherein the mammal is a human.

* * * * *